US010663450B2

(12) United States Patent
Tian et al.

(10) Patent No.: US 10,663,450 B2
(45) Date of Patent: May 26, 2020

(54) AMORPHOUS, POROUS SILICON MATERIALS AND RELATED METHODS

(71) Applicant: The University of Chicago, Chicago, IL (US)

(72) Inventors: Bozhi Tian, Chicago, IL (US); Francisco Bezanilla, Chicago, IL (US); Yuanwen Jiang, Chicago, IL (US); João L. Carvalho-de-Souza, Chicago, IL (US)

(73) Assignee: The University of Chicago, Chicago, IL (US)

( * ) Notice: Subject to any disclaimer, the term of this patent is extended or adjusted under 35 U.S.C. 154(b) by 281 days.

(21) Appl. No.: 15/623,133

(22) Filed: Jun. 14, 2017

(65) Prior Publication Data

US 2017/0363607 A1 Dec. 21, 2017

Related U.S. Application Data

(60) Provisional application No. 62/350,328, filed on Jun. 15, 2016.

(51) Int. Cl.
*C23C 16/01* (2006.01)
*G01N 33/483* (2006.01)
*C23C 16/24* (2006.01)
*G01N 33/50* (2006.01)
*C23C 16/04* (2006.01)

(52) U.S. Cl.
CPC ......... *G01N 33/4833* (2013.01); *C23C 16/01* (2013.01); *C23C 16/045* (2013.01); *C23C 16/24* (2013.01); *G01N 33/5014* (2013.01); *G01N 33/5061* (2013.01)

(58) Field of Classification Search
CPC ........... G01N 33/4833; G01N 33/5014; G01N 33/5061; C23C 16/01; C23C 16/045; C23C 16/24
USPC ........................................................ 428/402
See application file for complete search history.

(56) References Cited

U.S. PATENT DOCUMENTS

| | | | | |
|---|---|---|---|---|
| 3,301,635 A * | 1/1967 | Bergna | C04B 35/14 | 264/332 |
| 6,322,895 B1 * | 11/2001 | Canham | A61L 27/025 | 427/58 |
| 9,548,489 B2 * | 1/2017 | Abdelsalam | H01M 8/00 | |
| 9,765,271 B2 * | 9/2017 | Myrick | C06B 45/30 | |
| 2002/0155700 A1 * | 10/2002 | Chen | H01L 21/76831 | 438/639 |
| 2011/0163274 A1 * | 7/2011 | Plee | H01M 4/134 | 252/503 |
| 2011/0179071 A1 * | 7/2011 | Torr | H04L 67/42 | 707/769 |
| 2013/0266801 A1 * | 10/2013 | Sakannoto | B28B 11/24 | 428/338 |
| 2014/0079774 A1 * | 3/2014 | Brinker | C07K 14/47 | 424/450 |

FOREIGN PATENT DOCUMENTS

WO WO2012114126 8/2012

OTHER PUBLICATIONS

Chomski, E.&Ozin,G Panoscopic Silicon, Advanced Materials 12, 1071-1078, (2000).*
Bao,Z.H. et al. "Chemical reduction of three-dimentional silica micro-assemblies into microporous silicon replicas." Nature 446, 172-175, (2007).*
Arora, H., et al., "Block copolymer self-assambly-directed single-crystal . . .nanostructures." Science 330, 214-219, (2010).*
Richman, E. K. et al., "Ordered mesoporous silicon through magnesium reduction of polymer templated silica thin films." Nano Letters 8, 3075-3079, (2008).*
Shapiro et al. (Infrared light excites cells by changing their electrical capacitance, Nature. Comms. 3:3736, DOI: 10.1038, 2012) (Year: 2012).*
Caroll et al. (Microparticles with Bimodal Nanoporosity Derived by Microemulsion Templating, Langmuir, 2009, 25(23), 13540-13544 (Year: 2009).*
Isaiev et al., Thermal conductivity of partially amorphous porous silicon by photo acoustic technique, Materials Letters 128, Apr. 30, 2014, pp. 71-74.
Shen et al., Fabrication of high-quality amorphous silicon film from cyclopentasilane by vapor deposition between two parallel substrates, Chem. Commun. 51, Feb. 9, 2015, pp. 4417-4420.
Bao et al., Chemical reduction of three-dimensional silica micro-assemblies into microporous silicon replicas, Nature, vol. 446, Mar. 8, 2007, pp. 172-175.
Richman et al., Ordered Mesoporous Silicon through Magnesium Reduction of Polymer Templated Silica Thin Films, Nano Letters, vol. 8, No. 9, Aug. 15, 2008, pp. 3075-3079.
Ji et al., Gentle reduction of SBA-15 silica to its silicon replica with retention of morphology, RSC Adv. 4, Apr. 17, 2014, pp. 22048-22052.
Tian, B., et al., "Macroporous Nanowire Nanoelectronic Scaffolds for Synthetic Tissues", Nature Materials, Nov. 2012, vol. 11(11), pp. 986-994, doi:10.1038/nmat3404.

(Continued)

*Primary Examiner* — Alexandre F Ferre
(74) *Attorney, Agent, or Firm* — McDonnell Boehnen Hulbert & Berghoff LLP

(57) ABSTRACT

Provided herein are Si-based materials, methods of making the Si-based materials, and methods for using the Si-based materials. In embodiments, a silicon-based material comprises an aggregate of particles, the particles comprising an ordered array of nanostructures, the nanostructures comprising amorphous silicon, wherein at least some pairs of adjacent nanostructures are connected by one or more bridges comprising amorphous silicon, the one or more bridges extending from the surface of one nanostructure of the pair to the surface of the other nanostructure in the pair.

17 Claims, 18 Drawing Sheets

(56) References Cited

OTHER PUBLICATIONS

Wan, Y., et al., "Host-Guest Chemistry in the Synthesis of Ordered Nonsiliceous Mesoporous Materials", Accounts of Chemical Research, Jul. 2006, vol. 39(7), pp. 423-432, doi:10.1021/ar050091a.

Wegst, U.G.K., et al., "Bioinspired Structural Materials", Nature Materials, Jan. 2015, vol. 14, pp. 23-36, doi:10.1038/nmat4089.

Zhang, A.Q., et al., "Nano-Bioelectronics", Chemical Reviews, 2016, vol. 116, pp. 215-257, doi:10.1021/acs.chemrev.5b00608.

Zhao, D.Y., et al., "Triblock Copolymer Syntheses of Mesoporous Silica with Periodic 50 to 300 Angstrom Pores", Science, Jan. 23, 1998, vol. 279, pp. 548-552, doi:10.1126/science.279.5350.548.

Zimmerman, J.F., et al., "Free-Standing Kinked Silicon Nanowires for Probing Inter—and Intracellular Force Dynamics", Nano Letters, 2015, vol. 15, pp. 5492-5498, doi:10.1021/acs.nanolett.5b01963.

Zink, B.L., et al., "Thermal Conductivity and Specific Heat of Thin-Film Amorphous Silicon", Physical Review Letters, 2006, vol. 96, pp. 055902-1-055902-4, doi:10.1103/PhysRevLett.96.055902.

Arora, H., et al., "Block Copolymer Self-Assembly-Directed Single-Crystal Homo—and Heteroepitaxial Nanostructures", Science, Oct. 8, 2010, vol. 330, pp. 214-219, doi:10.1126/science.1193369.

Barisik, M., et al., "Temperature Dependence of Thermal Resistance at the Water/Silicon Interface", International Journal of Thermal Sciences, 2014, vol. 77, pp. 47-54, doi:10.1016/j.ijthermalsci.2013.10.012.

Bellet, D., et al., "Nanoindentation Investigation of the Young's Modulus of Porous Silicon", Journal of Applied Physics, 1996, vol. 80, pp. 3772-3776, doi:10.1063/1.363305.

Cahill, D.G., et al., "Thermal Conductivity of A-Si: H Thin Films", Physical Review B, 1994, vol. 50, pp. 6077-6081, doi:10.1103/PhysRevB.50.6077.

Carvalho-de-Souza, J.L., et al., "Photosensitivity of Neurons Enabled by Cell-Targeted Gold Nanoparticles", Neuron, Apr. 8, 2015, vol. 86(1), pp. 207-217, doi:10.1016/j.neuron.2015.02.033.

Chiappini, C., et al., "Biodegradable Silicon Nanoneedles Delivering Nucleic Acids Intracellularly Induce Localized in Vivo Neovascularization", Nature Materials, 2015, vol. 14, pp. 532-539, doi:10.1038/nmat4249.

Chomski, E., et al., "Panoscopic Silicon—A Material for "All" Length Scales", Advanced Materials, 2000, vol. 12, pp. 1071-1078, doi:10.1002/1521-4095(200007)12:14<1071::aid-adma1071>3.0.co;2-j.

Cogan, S.F., "Neural Stimulation and Recording Electrodes", Annual Review of Biomedical Engineering, 2008, vol. 10, pp. 275-309, doi:10.1146/annurev.bioeng.10.061807.160518.

Dai, F., et al., "Bottom-Up Synthesis of High Surface Area Mesoporous Crystalline Silicon and Evaluation of its Hydrogen Evolution Performance", Nature Communications, 2014, vol. 5(3605), pp. 1-11, doi:10.1038/ncomms4605.

Freund, L.B., et al., Thin Film Materials: Stress, Defect Formation and Surface Evolution, 1st edn, (Cambridge University Press, 2009). (Abstract only).

Gautieri, A., et al., "Hierarchical Structure and Nanomechanics of Collagen Microfibrils from the Atomistic Scale Up", Nano Letters, 2011, vol. 11, pp. 757-766, doi:10.1021/nl103943u.

Ghezzi, D., et al., "A Hybrid Bioorganic Interface for Neuronal Photoactivation", Nature Communications, 2011, vol. 2 (166), pp. 1-7, doi:10.1038/ncomms1164.

Gordon, L.M., et al., "Amorphous Intergranular Phases Control the Properties of Rodent Tooth Enamel", Science, Feb. 13, 2015, vol. 347(6223), pp. 746-750, doi:10.1126/science.1258950.

Gu, L., et al., "In Vivo Time-Gated Fluorescence Imaging with Biodegradable Luminescent Porous Silicon Nanoparticles", Nature Communications, 2013, vol. 4(2326), pp. 1-15, doi:10.1038/ncomms3326.

Gu, D., et al., "Synthesis of Non-Siliceous Mesoporous Oxides", Chemical Society Reviews, 2014, vol. 43, pp. 313-344, doi:10.1039/c3cs60155b.

Han, D.X., et al., "Raman Study of Thin Films of Amorphous-To-Microcrystalline Silicon Prepared by Hot-Wire Chemical Vapor Deposition", Journal of Applied Physics, 2003, vol. 94, pp. 2930-2936, doi:10.1063/1.1598298.

Hochbaum, A.I., et al., "Single Crystalline Mesoporous Silicon Nanowires", Nano Letters, 2009, vol. 9, pp. 3550-3554, doi:10.1021/nl9017594.

Hwang, S.-W., et al., "A Physically Transient Form of Silicon Electronics", Science, 2012, vol. 337, pp. 1640-1644, doi:10.1126/science.1226325.

Imperor-Clerc, M., et al., "Existence of a Microporous Corona Around the Mesopores of Silica-Based SBA-15 Materials Templated by Triblock Copolymers", Journal of the American Chemical Society, 2000, vol. 122, pp. 11925-11933, doi:10.1021/ja002245h.

Joo, S.H., et al., "Ordered Nanoporous Arrays of Carbon Supporting High Dispersions of Platinum Nanoparticles", Nature, 2001, vol. 412, pp. 169-172, doi:10.1038/35084046.

Kaplan, D.T., et al., "Subthreshold Dynamics in Periodically Stimulated Squid Giant Axons", Physical Review Letters, 1996, vol. 76, pp. 4074-4077, doi:10.1103/PhysRevLett.76.4074.

Karzbrun, E., et al., "Programmable On-Chip DNA Compartments as Artificial Cells", Science, 2014, vol. 345, pp. 829-832, doi:10.1126/science.1255550.

Katiyar, A., et al., "Synthesis of Ordered Large Pore SBA-15 Spherical Particles for Adsorption of Biomolecules", Journal of Chromatography A, 2006, vol. 1122, pp. 13-20, doi:10.1016/j.chroma.2006.04.055.

Kim, W., et al., "Interfacing Silicon Nanowires with Mammalian Cells", Journal of the American Chemical Society, 2007, vol. 129, pp. 7228-7229, doi:10.1021/ja071456k.

Kim, D.-H., et al., "Dissolvable Films of Silk Fibroin for Ultrathin Conformal Bio-Integrated Electronics", Nature Materials, 2010, vol. 9, pp. 511-517, doi:10.1038/nmat2745.

Kim, D.-H., et al., "Flexible and Stretchable Electronics for Biointegrated Devices", Annual Review of Biomedical Engineering, 2012, vol. 14, pp. 113-128, doi:10.1146/annurev-bioeng-071811-150018.

Kleitz, F., et al., "Cubic Ia3d Large Mesoporous Silica: Synthesis and Replication to Platinum Nanowires, Carbon and Carbon Nanotubes", Chemical Communications, 2003, pp. 2136-2137, doi:10.1039/b306504a. Nanorods.

Kovalev, D., et al., "The Temperature Dependence of the Absorption Coefficient of Porous Silicon", Journal of Applied Physics, 1996, vol. 80, pp. 5978-5983, doi:10.1063/1.363595. (Abstract only).

Lanzani, G., "Materials for Bioelectronics: Organic Electronics Meets Biology", Nature Materials, 2014, vol. 13, pp. 775-776.

Leigh, C., Handbook of Porous Silicon, 1st edn, (Springer, 2014). (Abstract only).

Li, L., et al., "Multifunctionality of Chiton Biomineralized Armor with an Integrated Visual System", Science, 2015, vol. pp. 952-956, doi:10.1126/science.aad1246. 350,.

Li, X., et al., "Metal-Assisted Chemical Etching in Hf/H(2)O(2) Produces Porous Silicon", Applied Physics Letters, vol. 77, pp. 2572-2574, doi:10.1063/1.1319191. 2000,.

Liu, J., et al., "Syringe-Injectable Electronics", Nature Nanotechnology, 2015, vol. 10, pp. 629-636, doi:10.1038/ nnano.2015.115.

Liu, Y., et al., "Dopamine-Melanin Colloidal Nanospheres: an Efficient Near-Infrared Photothermal Therapeutic Agent for in Vivo Cancer Therapy", Advanced Materials, 2013, vol. 25, pp. 1353-1359, doi:10.1002/adma.201204683.

Liu, Y., et al., "Polydopamine and its Derivative Materials: Synthesis and Promising Applications in Energy, Environmental, and Biomedical Fields", Chemical Reviews, May 14, 2014, vol. 114(9), pp. 5057-5115, doi:10.1021/ cr400407a, Epub 2014 Feb 11. (Abstract only).

McGuire, G.E., Semiconductor Materials and Process Technology Handbook, (William Andrew Publishing/Noyes, 1988). (Abstract only).

Minev, I.R., et al., "Electronic Dura Mater for Long-Term Multimodal Neural Interfaces", Science, 2015, vol. 347, pp. 159-163, doi:10.1126/science.1260318.

(56) References Cited

OTHER PUBLICATIONS

Ott, H.C., et al., "Perfusion-Decellularized Matrix: Using Nature's Platform to Engineer a Bioartificial Heart", Nature Medicine, 2008, vol. 14, pp. 213-221, doi:10.1038/nm1684.
Pan, L., et al., "Hierarchical Nanostructured Conducting Polymer Hydrogel with High Electrochemical Activity", Proceedings of the National Academy of Sciences of the United States of America, 2012, vol. 109, pp. 9287-9292, doi:10.1073/pnas.1202636109.
Park, J.-H., et al., "Biodegradable Luminescent Porous Silicon Nanoparticles for in Vivo Applications", Nature Materials, 2009, vol. 8, pp. 331-336, doi:10.1038/nmat2398.
Picas, L., et al., "Direct Measurement of the Mechanical Properties of Lipid Phases in Supported Bilayers", Biophysical Journal, 2012, vol. 102, pp. L1-L3, doi:10.1016/j.bpj.2011.11.4001.
Qu, Y., et al., "Electrically Conductive and Optically Active Porous Silicon Nanowires", Nano Letters, 2009, vol. 9, pp. 4539-4543, doi:10.1021/nl903030h.
Sailor, M.J., Porous Silicon in Practice: Preparation, Characterization, and Applications, (Wiley-Vch: Weinheim, Germany, 2012). (Abstract only).
Sanders, a.W., et al., "Gold Nanoparticle Quantitation by Whole Cell Tomography", Acs Nano, 2015, vol. 9, pp. 11792-11799, doi:10.1021/acsnano.5b03815.
Sayari, A., et al., "Simple Synthesis Route to Monodispersed Sba-15 Silica Rods", Journal of the American Chemical Society, 2004, vol. 126, pp. 14348-14349, doi:10.1021/ja0478734.
Shapiro, M.G., et. al., "Infrared Light Excites Cells by Changing their Electrical Capacitance", Nature Communications, 2012, vol. 3(736), pp. 1-11, doi:10.1038/ncomms1742.
Tanaka, K., et al., Amorphous Silicon, 1st edn, (Wiley, 1999). (Abstract only).
Tasciotti, E., et al., "Mesoporous Silicon Particles as a Multistage Delivery System for Imaging and Therapeutic Applications", Nature Nanotechnology, Mar. 2008, vol. 3, pp. 151-157, doi:10.1038/nnano.2008.34.
Tee, B.C.K., et, al., "A Skin-Inspired Organic Digital Mechanoreceptor", Science, Oct. 16, 2015, vol. 350(6258), pp. 313-316, doi:10.1126/science.aaa9306.
Tian, B., et al., "Synthetic Nanoelectronic Probes for Biological Cells and Tissues", Annual Review of Analytical Chemistry, 2013, vol. 6, pp. 31-51, doi:10.1146/annurev-anchem-062012-092623.

* cited by examiner

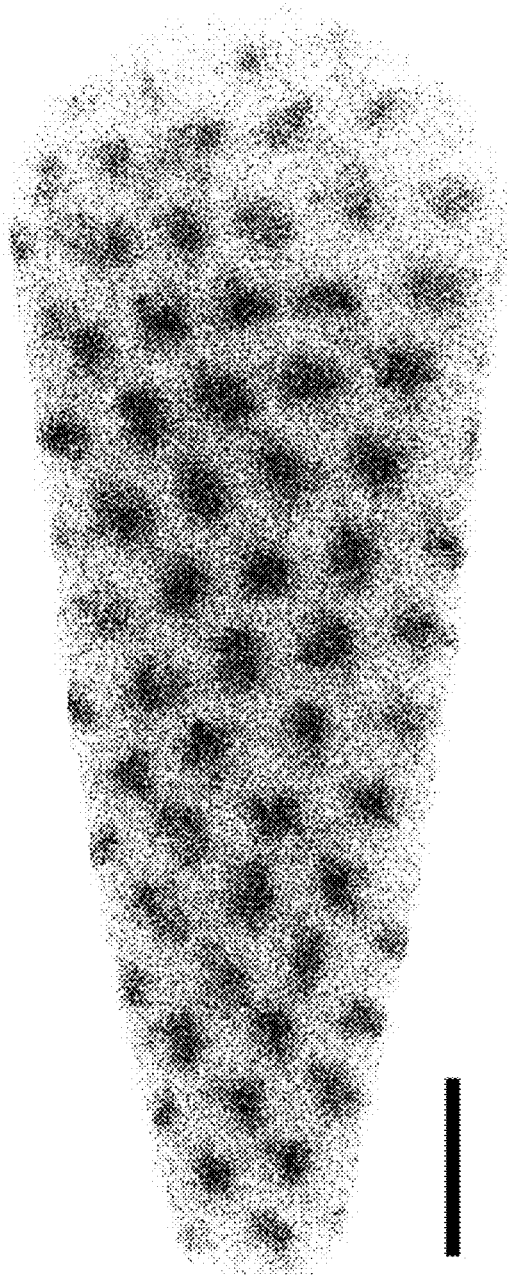
FIG. 2A
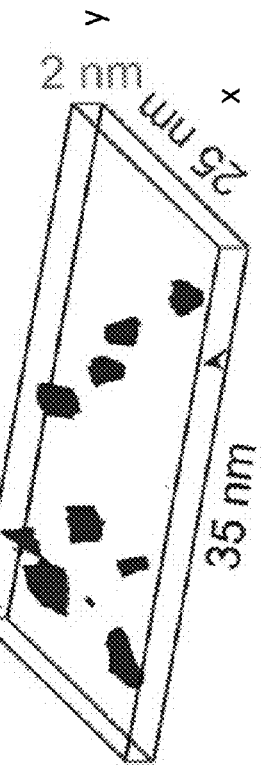
FIG. 2C
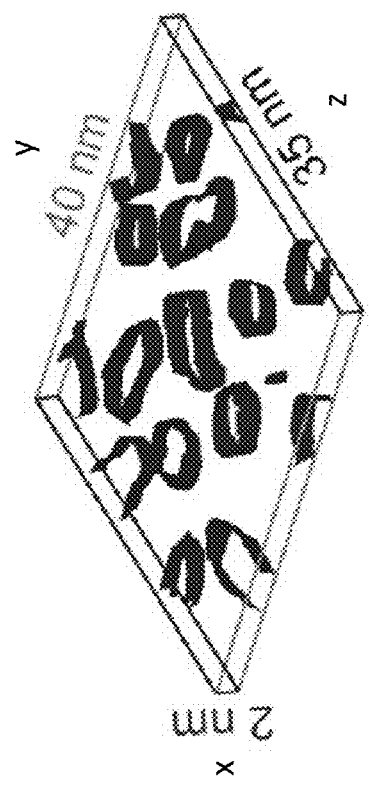

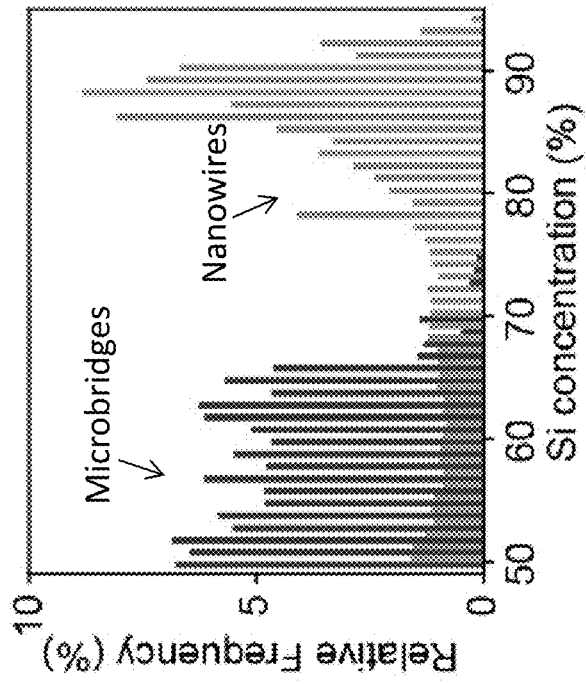
FIG. 2D
FIG. 2E
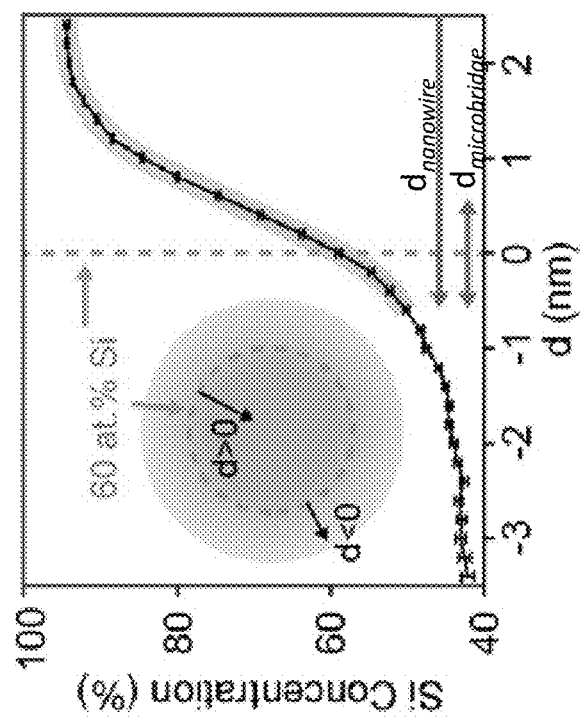
FIG. 2F
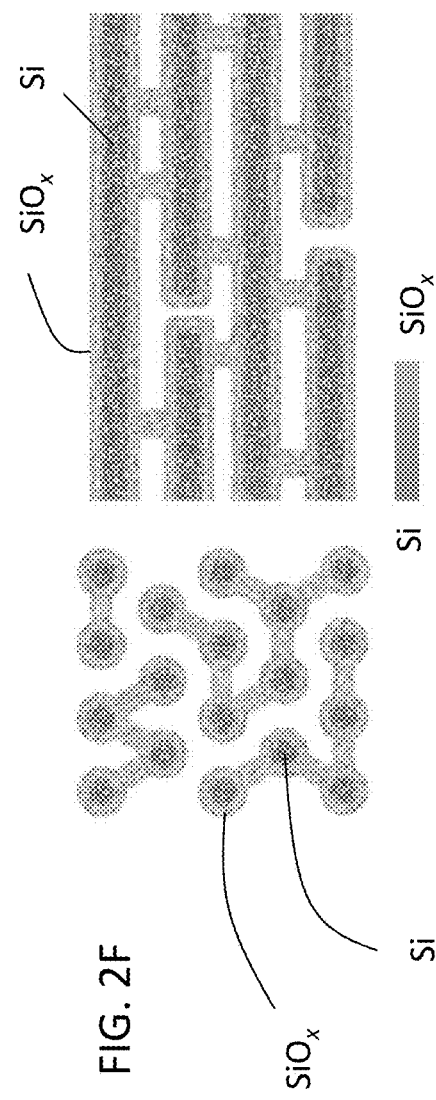

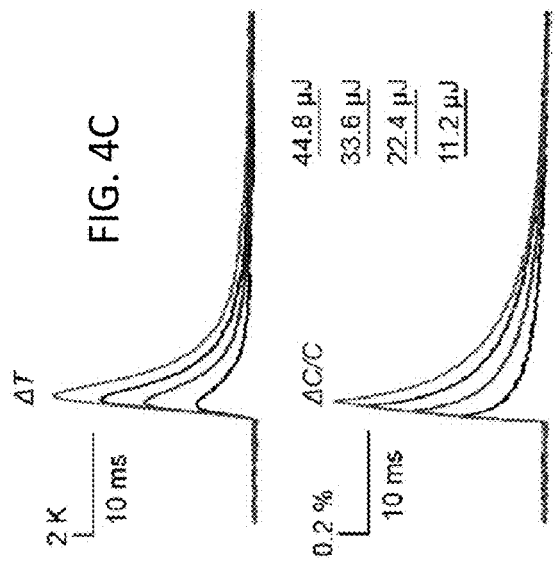
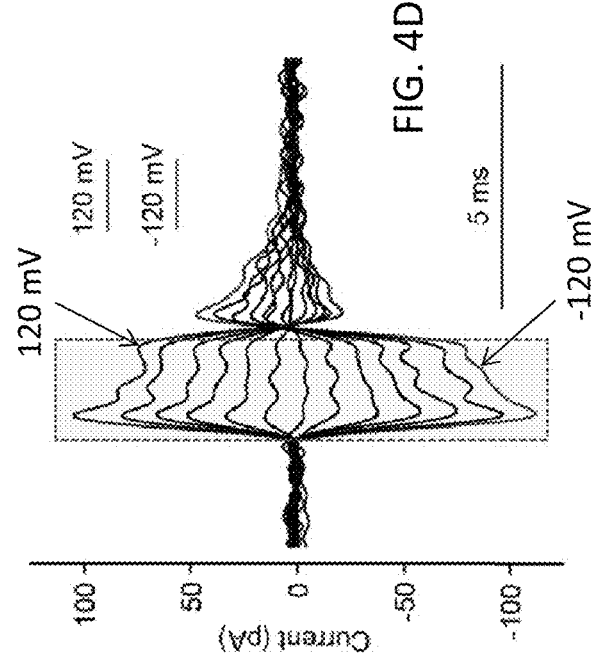
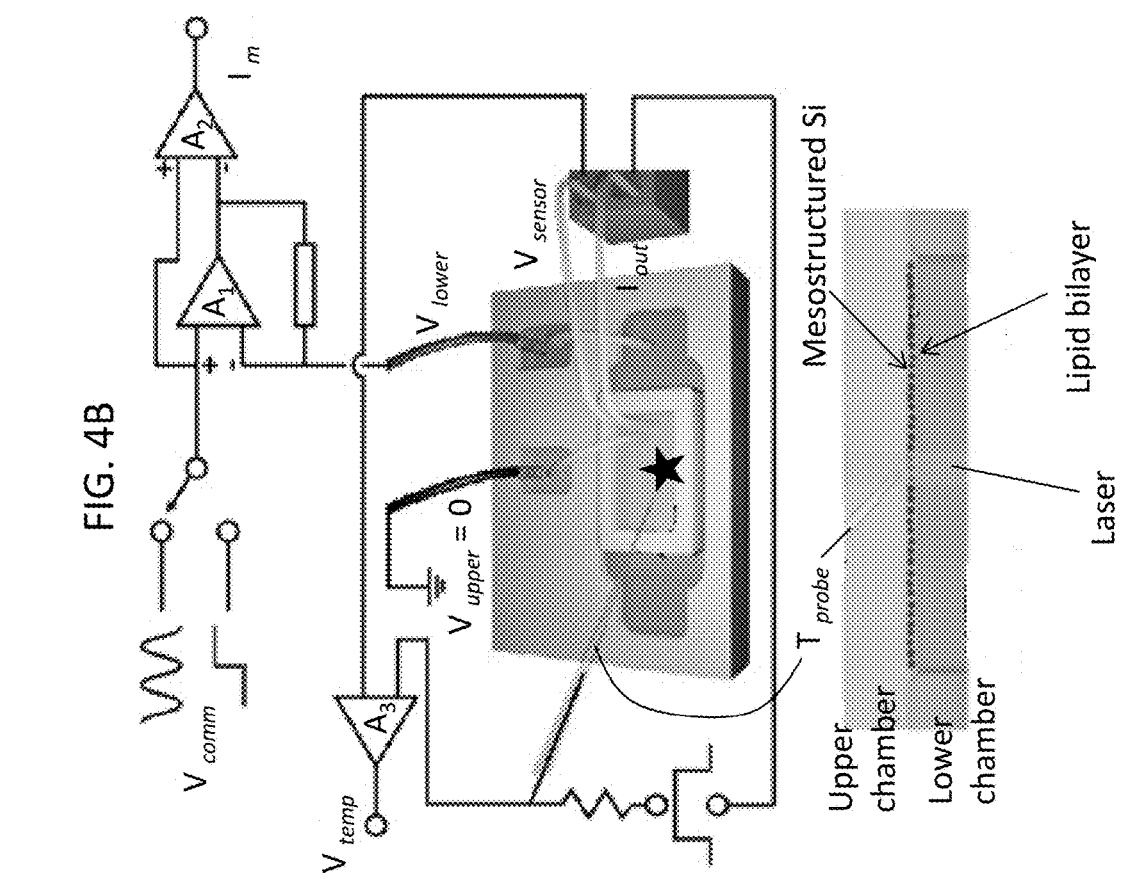

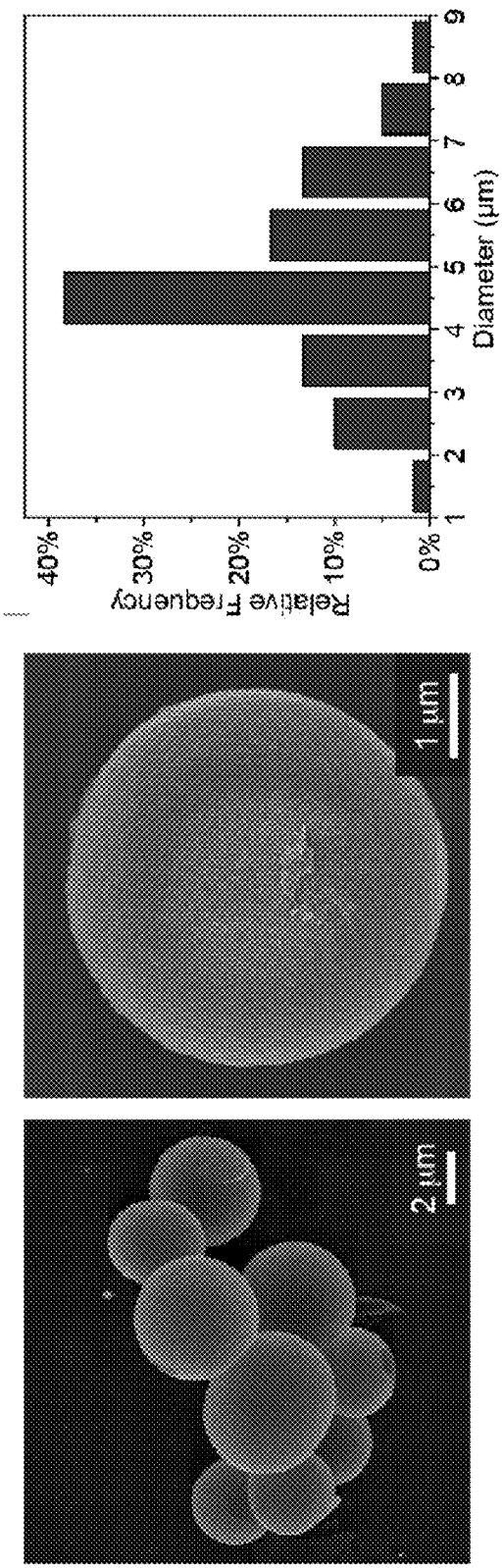

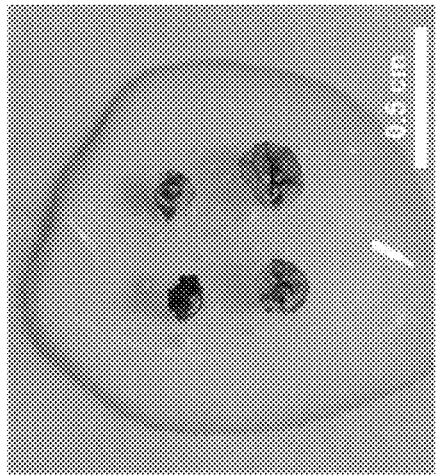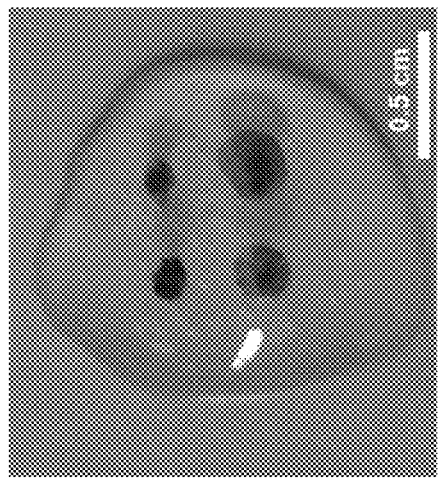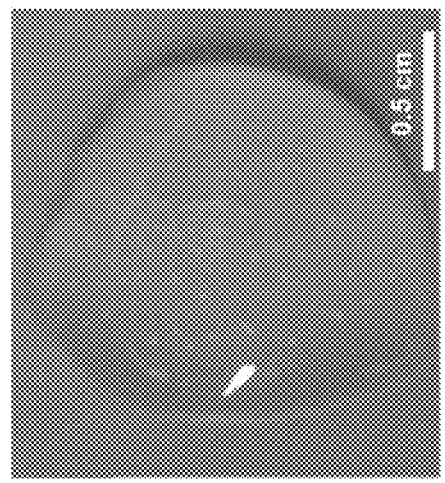
FIG. 8C

AMORPHOUS, POROUS SILICON MATERIALS AND RELATED METHODS

CROSS-REFERENCE TO RELATED APPLICATIONS

The present application claims priority from U.S. provisional patent application No. 62/350,328, which was filed on Jun. 15, 2016, the entire contents of which are hereby incorporated by reference.

REFERENCE TO GOVERNMENT RIGHTS

This invention was made with government support under FA9550-14-1-0175 and FA9550-15-1-0285 awarded by the Air Force Office of Scientific Research, under DMR-1254637 and DMR-1420709 awarded by the National Science Foundation, and under GM030376 awarded by the National Institutes of Health. The government has certain rights in the invention.

BACKGROUND

Silicon (Si) is a widely used material in biomedical research[1-11] because it is biocompatible and biodegradable, and it exhibits a spectrum of important electrical, optical, thermal and mechanical properties. For example, Si-based systems can sense electrical activities of the brain in flexible and adhesive configurations[12-14], deliver nucleic acids in vivo to induce angiogenesis[7], and perform intra- and intercellular force dynamics measurements[15]. So far, most of the applications of Si as biomaterials have been focused on or originated from single crystalline structures or substrates, which is primarily due to the need for high quality and controllable electrical or other properties. Natural biomaterials have remarkable diversity in structure and function and have informed the design[16] of new Si forms[17-22] for subcellular interfaces and biophysical modulation (FIG. 1A, top). While nano-casting synthesis of mesoporous solids is highly versatile and scalable, ordered and freestanding Si-based mesostructures with molecular-level principal feature sizes (i.e., <10 nm) are still challenging to achieve[17,18,27,30].

SUMMARY

Provided herein are Si-based materials, methods of making the Si-based materials, and methods for using the Si-based materials.

In one aspect a silicon-based material is provided, the material comprising an aggregate of particles, the particles comprising an ordered array of nanostructures, the nanostructures comprising amorphous silicon, wherein at least some pairs of adjacent nanostructures are connected by one or more bridges comprising amorphous silicon, the one or more bridges extending from the surface of one nanostructure of the pair to the surface of the other nanostructure in the pair. Single particles of this silicon-based material are also provided.

In another aspect, a method of making a silicon-based material is provided, the method comprising exposing a mesoporous silica template to a silicon precursor under conditions to deposit silicon on the surfaces of the mesoporous silica template via chemical vapor deposition (CVD); and removing the mesoporous silica template to provide the silicon-based material.

In another aspect, a method of using a silicon-based material is provided, the method comprising positioning the silicon-based material or a single particle of the material in the vicinity of a lipid bilayer; and illuminating the silicon-based material or the single particle with light to produce a photothermal response in the silicon-based material or the single particle. The silicon-based material may comprise an ordered aggregate of particles, the particles comprising an ordered array of nanostructures, the nanostructures comprising amorphous silicon, wherein at least some pairs of adjacent nanostructures are connected by one or more bridges comprising amorphous silicon, the one or more bridges extending from the surface of one nanostructure of the pair to the surface of the other nanostructure in the pair.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

In the description of the drawings below, as well as throughout the disclosure, "mesostructured Si" and "Si-based material" are used interchangeably.

FIG. 1A shows that Si-based cellular modulation materials can be designed to share similar mesostructures with natural biomaterials, e.g., bones, with ordered unidirectional fibril networks that are maintained by molecular cross-links.

FIG. 1B shows the double quartz-tubing system used for nano-casting synthesis, with a mesoporous $SiO_2$ template placed near the bottom of the inner tube (left). After HF etching, the brownish product (right) is obtained. Scale bars, 1 cm.

FIG. 1C shows a scanning electron microscope (SEM) image of as-synthesized Si particles showing a morphology similar to that of the SBA-15 template. Scale bar, 2 µm.

FIG. 1D shows a transmission X-ray microscopy (TXM) 3D dataset of a representative region of mesostructured silicon (left). A thin slice of the dataset (lines) highlights the presence of both intra- and inter-granular voids (right). Representing silicon as a semi-transparent matrix allows clearer visualization of the voids (upper right). Darker regions in the upper right image correspond to intra-granular voids; open regions in the whole volume or thin slice correspond to inter-granular voids.

FIG. 1E is a small angle X-ray scattering (SAXS) profile showing mesoscale periodicity with a 2D hexagonal symmetry.

FIG. 1F is a SEM image revealing the periodic arrangement of the Si nanowire assembly. Scale bar, 100 nm.

FIG. 1G is a transmission electron microscope (TEM) image (left) and its FFT diffractogram (lower right) indicating the hexagonal packing of Si nanowires (left panel). The (selected area electron diffraction) SAED pattern shows an amorphous atomic structure (upper right). Scale bar, 100 nm.

FIGS. 2A-2F illustrate the size-dependent chemical heterogeneity of mesostructured Si. FIG. 2A shows an atom probe tomography (APT) image of one as-deposited sample (i.e., without $SiO_2$ removal) which exhibits the hexagonal packing of Si nanowires in $SiO_2$ matrix. For clarity, only 5% of total Si and O are displayed. Scale bar, 20 nm.

FIG. 2B shows the 60 at. % (upper) and 75 at. % (lower) Si isoconcentration surfaces viewed from x (left) and z (right) directions. The presence of micro-bridges (arrow) in 60 at. % surfaces (upper) and their absence in 75 at. % surfaces (lower) shows that the overall Si concentration is less in micro-bridges than in Si nanowires. Scale bars, 10 nm.

FIG. 2C shows representative slices showing Si nanowires (left) and micro-bridges (right) separately, rendered as 65 at. % Si isoconcentration surfaces. Lines and numbers denote dimensions along x, y and z axes.

FIGS. 2D and 2E show proximity histogram concentration profiles (FIG. 2D) and Si concentration distribution histograms (FIG. 2E) confirming the size-dependent Si concentration in Si nanowires and micro-bridges. 'd' in FIG. 2D denotes the distance from the 60 at. % Si isoconcentration surfaces and a positive/negative value means that the point is inside/outside the enclosed isoconcentration surface. The curved thick lines estimate the decoupled Si distributions in micro-bridges and nanowires, respectively, given the different principal feature sizes in these two components (lines with arrows).

FIG. 2F shows side- (right) and end-view (left) schematics of mesostructured Si illustrating the graded $Si/SiO_x$ interfaces and the observed chemical heterogeneity between nanowires and micro-bridges.

FIG. 3A shows a box-and-whisker plot of Young's moduli of mesostructured Si measured in air and in a PBS solution. Half of the data points are within the boxes, 80% are within the whiskers. Solid and dashed lines represent the medians and means, respectively. The dots mark the maximum and minimum values. n=138 for measurement in air, n=94 in PBS. The number above the bar is the p-value of the Mann-Whitney test.

FIG. 3B shows Raman spectrum and FIG. 3C shows UV-vis spectrum of mesostructured Si submerged in PBS for 0 h and 24 h. The dashed line in FIG. 3B marks the position of Transverse Optical peak, whose position and width reflect the distribution of bond angle (θ). Extrapolation from Tauc plots (FIG. 3C, right) of the UV-vis spectra yield band gaps. Raman and UV-vis spectra were collected in PBS and air, respectively.

FIG. 3D shows a cross-sectional TEM image of a representative mesostructured Si/human umbilical vein endothelial cell (HUVEC) interface after freeze-substitution and resin embedding. The dashed box marks the region for a zoom-in view on the right. The nanowires ends are marked with dots. Scale bars, 100 nm (left), 20 nm (right).

FIG. 3E shows a schematic diagram (upper left) of the single-cell calcium imaging assay, with relative amplitude ($\Delta F/F_0$) and slope (($dF/dt)/F_0$) defined (lower left). A scattered plot (right) for the amplitude and slope values of the calcium dynamics, recorded from porous/mesostructured/ amorphous (squares) and solid/single crystalline (circles) particles. Insets display 2D distribution histograms associated with porous (upper left) and solid (lower right) samples. n=44 for each group.

FIGS. 4A-4G show an illustrative use of mesostructured Si, involving a remotely actuated and lipid-supported bioelectric interface as a dynamic hybrid system. FIG. 4A shows the schematics of a light actuated bioelectric interface (top), where transient capacitive currents across lipid bilayer (LB) are generated due to the photothermal effect of mesostructured Si. A hybrid Si/cell system (bottom) uses pulsed optical signals as the input (i) and yields local transient heating. The fast transient heating generates capacitive currents through LB (ii) which, together with the currents passing through ion channels (iv), determine the membrane potential. The ion channel activities can be affected by the membrane potential (v) which is the result of either ionic currents and/or of the change in membrane capacitance by transient heating but also by direct heating (iii). All these processes integrate together as a single dynamic hybrid system, generating output (vi) that is recognizable in time and frequency domains and as 2D maps.

FIG. 4B illustrates a planar and remotely controlled bioelectric interface made from densely packed Si mesostructures and an artificial lipid bilayer. Experimental setup (top) shows measurements of local solution temperature, bilayer electrical capacitance, and membrane current, upon localized laser illumination at the Si/lipid interface (top panel). The star marks a drilled hole at the bottom of top chamber, where lipid bilayer forms. Two independent circuits are shown. The first circuit uses $A_1$ and $A_2$ as a patch clamp that measures membrane currents ($I_m$) in response to a command voltage ($V_{comm}$) clamped at $V_{lower}$, connected to the solution pool below the bilayer. $V_{comm}$ can be conventional voltage pulses or a sinusoidal voltage signal. $V_{upper}$ connects the pool on top of the chamber to ground. The second circuit, using $A_3$, records a voltage drop ($V_{temp}$) between the pipette ($T_{probe}$) and $V_{sensor}$, in response to a current applied between the pipette and $I_{out}$. $V_{temp}$ is proportional to the pipette resistance, which in turn is a function of the temperature (see the Example, below). A zoom-in side view of the setup (bottom) shows Si/lipid interface.

FIG. 4C shows the averaged local solution temperature (top) and bilayer capacitance (bottom) dynamics upon laser pulses with different input energies (highest input energy top curve, lowest input energy bottom curve). n=50.

FIG. 4D shows capacitive currents in response to laser pulses (44.8 µJ), recorded in voltage-clamp mode. Traces indicate the currents when the potentials were clamped at −120 mV (lowest trace) and 120 mV (uppermost trace), respectively. Middle traces are recordings at intermediate potentials in increments of 20 mV. Bar indicates when laser pulse was on. n=10.

FIG. 4E shows the experimental setup used to elicit action potentials in dorsal root ganglia (DRG) neurons by illuminating a single Si particle attached to a cell. Neurons were patch clamped in the current-clamp whole-cell mode. AOM, acousto-optic modulator; ND, neutral density filters; DIC, dichroic mirror; OBJ, microscope objective; AMP, amplifier; LPF, low-pass filter; ADC, analog-to-digital converter. Inset shows that a portion of the cell membrane functions as a built-in device.

FIG. 4F shows representative intracellular potential recordings of a DRG neuron to trains of laser pulses (5.32 µJ) at different frequencies, with corresponding FFTs (right). f and $f_0$ are output and input frequencies, respectively. Lower ticks indicate when laser pulses were delivered. FIG. 4G shows an area-based return map which reveals an evolution of frequency-dependent 2-D patterns. Data points are analyzed from 20 spikes per trial, 4 trials per frequency.

FIGS. 5A-5B illustrate sphere-like mesostructured Si. FIG. 5A shows SEM images and FIG. 5B shows the diameter distribution the particles of the material. The spheres were synthesized using cetyltrimethylammonium bromide (CTAB) as a co-surfactant and ethanol as a co-solvent.

FIG. 7A shows SEM images and FIG. 7B shows TEM images. FIG. 7C shows the width and length distributions.

FIGS. 8A-8C show illustrative formulations for mesostructured Si. FIG. 8A shows that the mesostructured Si can be molded (upper) after mixing with water to form clay-like pastes. The shaped part can be further indented (lower). White dots with different sizes (lower) mark the surface indentations with different depths. Scale bars, 1 cm.

FIG. 8B shows that mesostructured Si forms suspensions when mixed and sonicated with solvent (isopropanol, water, etc.) and can be drop-casted on substrates to yield continuous thin films (upper). SEM image of an as-deposited Si film (lower) shows interconnected gel-like network, reminiscent of xerogel surfaces. The individual particles exhibit rod-like morphology (star, and corresponding zoom-in view in the upper box) and characteristic curvature (star, and the corresponding zoom-in view in the lower box), consistent with those in SBA-15 template.

FIG. 8C shows that mesostructured Si can be injected with syringe into a collagen hydrogel (left and middle panels, 2.98 mg/mL collagen). Only minor expansion of Si spots was observed after post-injection incubation at 37° C. for 18 h (right), indicating good retention of the material within fibrous biological matrix (right).

FIG. 9A (upper) shows a double-tube deposition chamber having an inner quartz tube. Although the deposition time is longer (e.g., 2 h), the sample morphology is uniform and there is a minimum sample loss (and correspondingly minimum contamination to vacuum system). By contrast, in an inner quartz boat (FIG. 9A, lower) has a much larger opening and allows shorter Si deposition duration (e.g., 30 min). However, the sample uniformity is poor and some regions showed solid Si shell coatings.

FIG. 9B shows the SEM images of particles with solid Si shell coatings, formed in certain regions when an inner quartz boat was used as the sample container. The broken area (right) suggests that there were still nanowire bundles inside the shells. One significant issue with an inner quartz boat is the sample loss during Si deposition, which can contaminate the CVD system.

DETAILED DESCRIPTION

Provided herein are Si-based materials, methods of making the Si-based materials, and methods for using the Si-based materials. By "Si-based" it is meant that the materials are composed primarily of silicon, although they may include an amount of another element, e.g., oxygen. The Si-based materials are characterized by both structural and chemical heterogeneity, which influences the mechanical, optical, thermal and electrical properties of the Si-based materials. The properties of illustrative embodiments of the Si-based materials are listed in Table 1, below. These properties render the Si-based materials useful for a wide range of applications, as described below.

TABLE 1

Characteristics of a Si-based material according to an illustrative embodiment.

| Length Scale | Structural | Chemical | Mechanical | Optical | Thermal | Electrical |
|---|---|---|---|---|---|---|
| atomic | Amorphous matrix | | Compared to crystalline Si, amorphous phase has lower Young's modulus. | Compared to crystalline Si, amorphous phase has larger absorptivity. | Compared to crystalline Si, amorphous phase has lower thermal conductivity/diffusivity. | |
| <2 nm | Random micro-bridges | O-rich | Hydration and degradation of ultrathin O-rich micro-bridges can help produce soft surface layers in saline. | | O-rich components can improve thermal stability. | |
| ~10 nm | Ordered nanowire arrays | Si-rich | The porous frame work can reduce Young's modulus. | The porous framework can improve light trapping. | The porous frame work can lower thermal conductivity/diffusivity. | Provide long-range electrical conductivity. |
| 0.2~1 μm | Irregular inter- and intra-granular voids | | | | | |
| The whole particle (1~10 μm) | Multi-scale structural heterogeneity | Size-dependent chemical heterogeneity | Young's modulus is 2-3 orders of magnitude less than that of bulk Si. | | | Electrically conductive across single particles. |
| The whole particle (1~10 μm) | Multi-scale structural heterogeneity | Size-dependent chemical heterogeneity | Young's modulus is 2-3 orders of magnitude less than that of bulk Si. | Fast photothermal effect that induces capacitive currents for lipid bilayer-supported bioelectric interfacing. Thermally stable | | Electrically conductive across single particles. |

Si-Based Materials

As will be further described, the methods of making the Si-based materials involve the use of a mesoporous silica ($SiO_2$) template. However, the steps of the methods described below show that the mesoporous silica template is used very differently as compared to conventional methods, e.g., those involving the reduction of a mesoporous silica template to convert the mesoporous silica to mesoporous silicon.

Figure 1A:
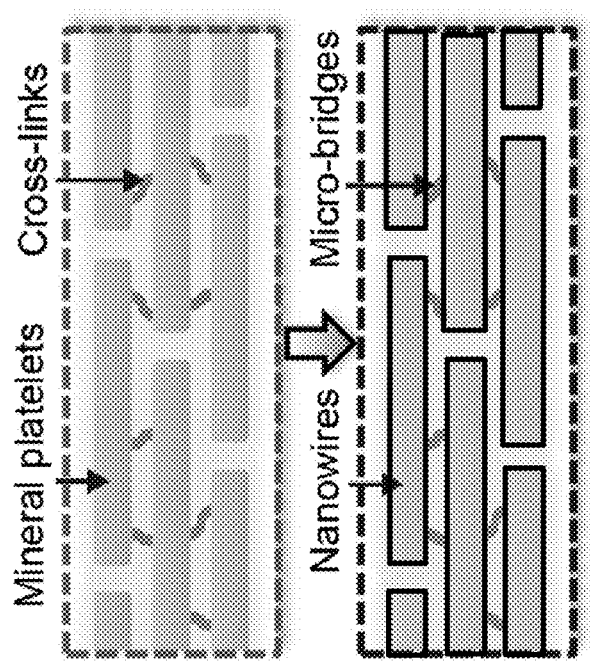
FIGS. 1A-1G illustrate the structural properties of the mesostructured Si material, showing that it can have multi-scale structural heterogeneity and ordered mesoscale features.
Figure 1B:
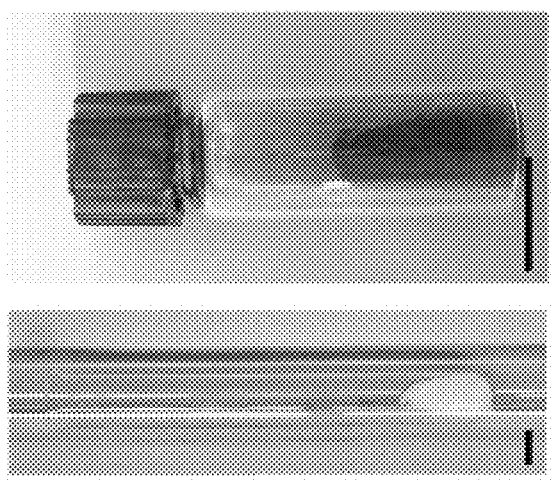

The present Si-based materials are both porous and, on the atomic scale, amorphous. By "amorphous silicon" it is meant that the silicon in the Si-base material does not exhibit any significant long-range order on the atomic scale, i.e., that the lack of crystalline order is on the atomic scale. This is evidenced by the absence of selected area electron diffraction (SAED) spots and the appearance of diffuse rings as shown in FIG. 1G. (The diffractogram also shown in FIG. 1G indicates the hexagonal packing of Si nanowires in this Si-based material, rather than crystallized Si.) Thus, throughout the present disclosure, the term "amorphous" may be used to describe a lack of crystalline order down to the atomic scale, i.e., over a length of about 1 nm and less.

Furthermore, confirmation of the amorphous nature of the Si-based materials may be accomplished via electron microscopy according to the techniques described in the Example, below. The amorphous nature of the Si-based materials is by contrast to materials in which the silicon atoms are ordered and exhibit crystalline order over lengths greater than about 1 nm, e.g., 10 nm, 20 nm, 30 nm or greater. Such materials are described as polycrystalline silicon, single crystalline silicon, monocrystalline silicon, crystalline silicon, etc.

Because of the unique methods of making the Si-based materials, they exhibit both structural and chemical heterogeneity, which influences their properties. The nature of this structural and chemical heterogeneity depends, in part, upon the mesoporous silica template used to form the Si-based material. The structure, chemistry and properties of illustrative Si-based materials are further described immediately below.

Particles of the Si-Based Material

Figure 6:
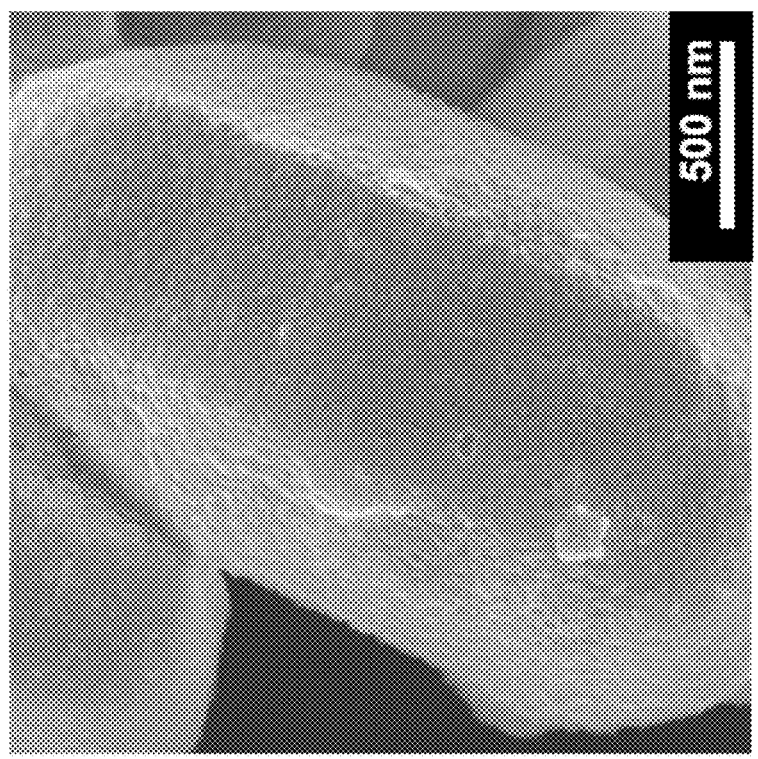
FIG. 6 shows a SEM image of a particle of wheat-shaped mesostructured Si synthesized at 600° C.
Figure 7C:
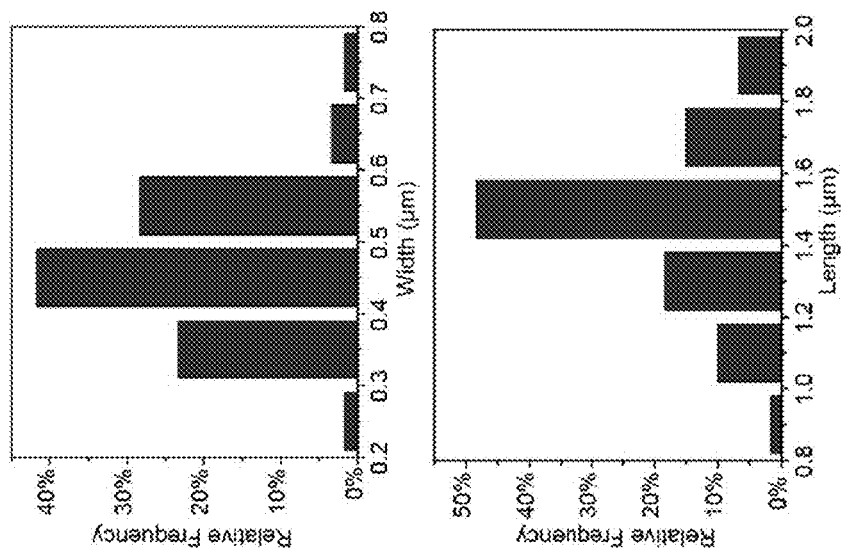
FIGS. 7A-7C illustrate rod-like mesostructured Si.
Figure 7A:
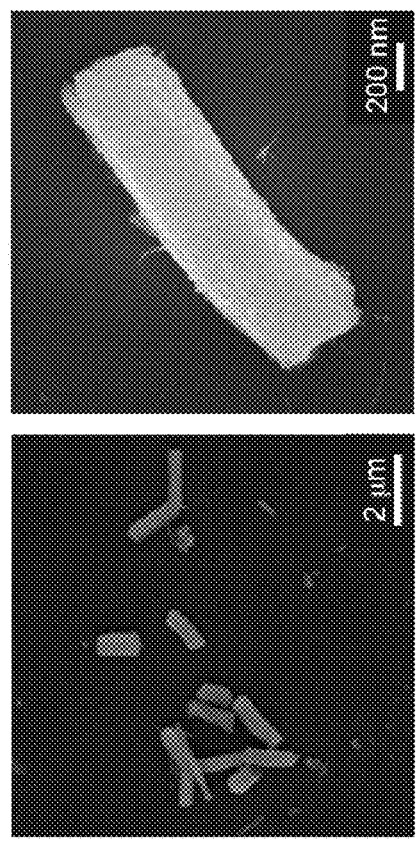
Figure 7B:
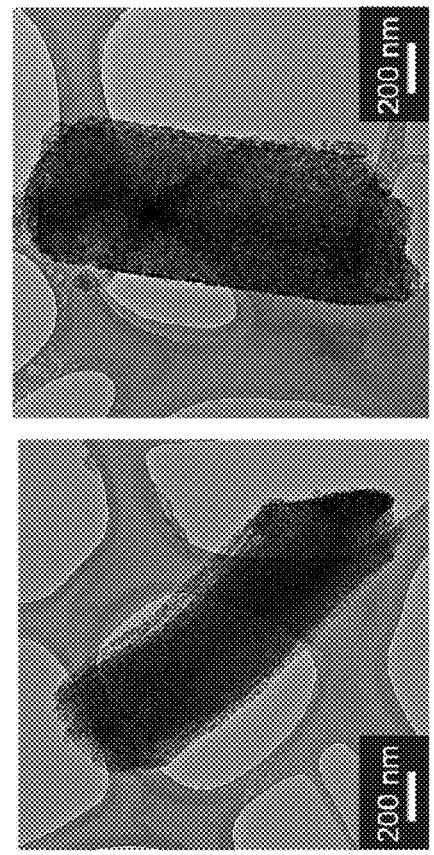

In embodiments, the Si-based material is composed of discrete, distinguishable particles (e.g., as visualized from electron microscopy images according to the techniques described in the Example below). The particles may assume a variety of shapes, e.g., spheres (see FIG. 5A), rods (see FIGS. 7A-7B), and shapes resembling grains of wheat (see FIG. 6). The "wheat-shaped" particles resemble the morphology of rod-shaped particles, but may have more rounded and/or tapered ends. Irregularly-shaped particles may also be used.

The particles of the Si-based material may have various dimensions, the magnitude of which may also be determined electron microscopy images according to the techniques described in the Example below. However, in embodiments, the particles are micron-sized, i.e., each of the dimensions of the particles is on the order of microns. Thus, the term "microparticle" may be used in this disclosure to describe the particles of the Si-based materials. The particles may have an average diameter in the range of from about 0.10 μm to about 100 μm, from about 0.25 μm to about 50 μm, from about 0.50 μm to about 25 μm, or from about 1 μm to about 10 μm. The "diameter" may also be referred to as a "width" for particles having a non-circular cross-section. In embodiments, the particles are elongated having a length which is greater than their diameter/width. Rod-shaped and wheat-shaped particles are examples of such particles. The average length of elongated particles may be in the range of from about 0.5 μm to about 100 μm, from about 1 μm to about 50 μm, or from about 1 μm to about 10 μm.

Figure 1C:
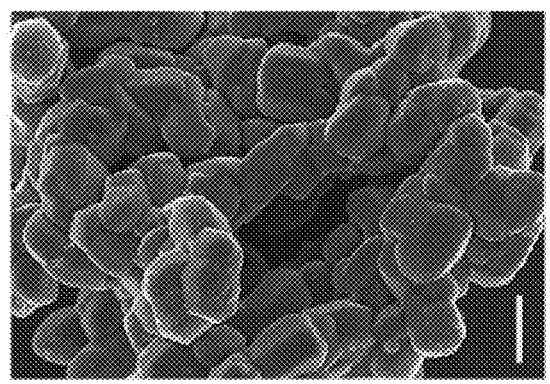
Figure 1E:
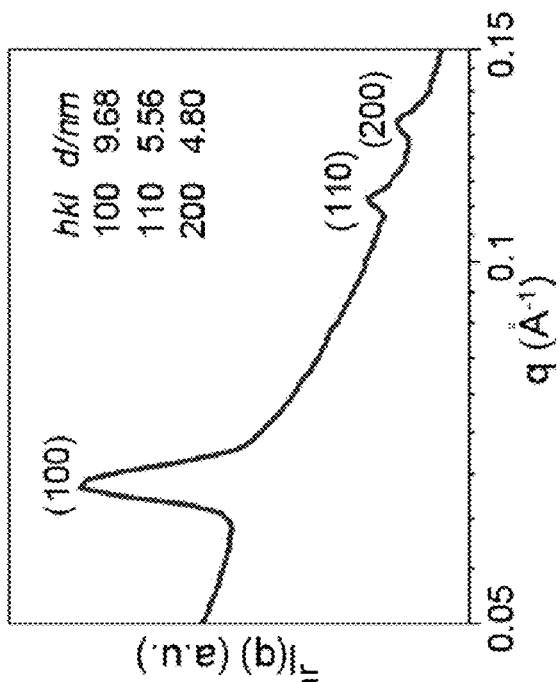
Figure 1D:
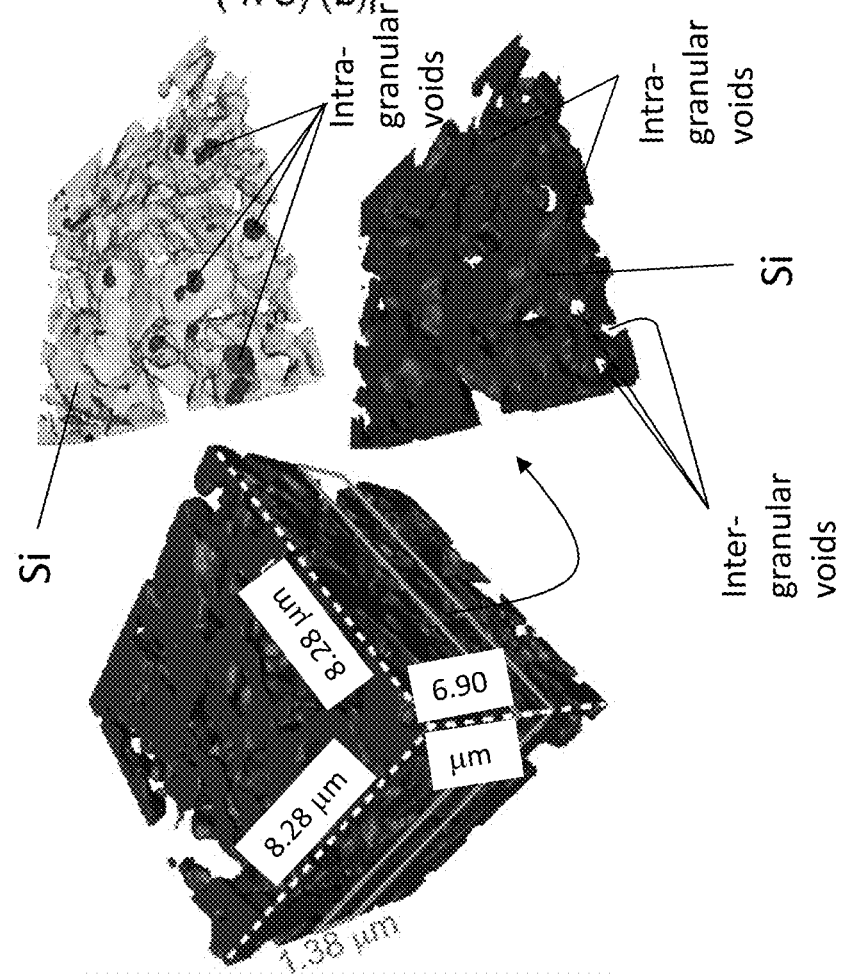
Figures 1F, 1G:
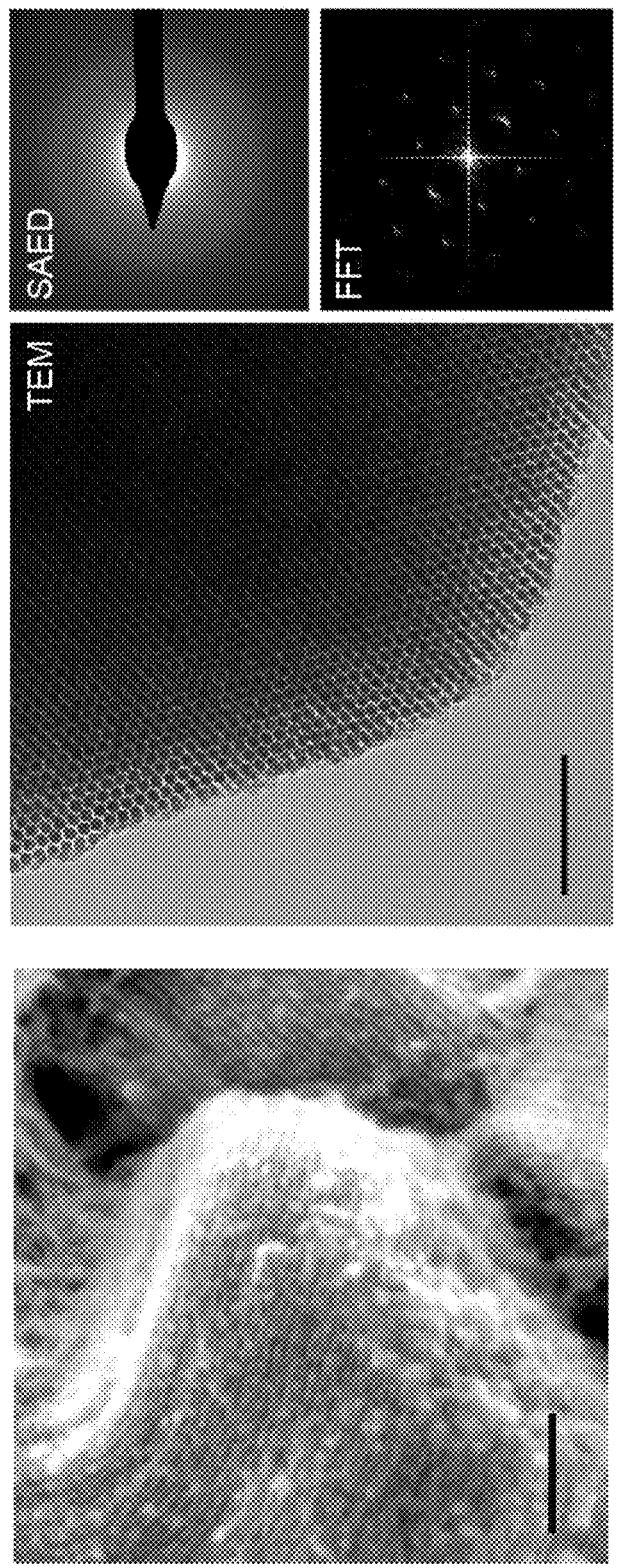

The particles may assemble together to form a larger, aggregate (see FIG. 1C, showing an aggregate of wheat-shaped particles). Within the aggregate, the particles may be randomly oriented. Particles may be in direct contact with one or more neighboring particles. In the aggregate, the outer surfaces of the particles define a plurality of irregularly shaped pores randomly distributed throughout the material. Such pores may be referred to as "intergranular voids" in this disclosure (see FIG. 1D). The individual particles themselves may also have pores defined therein, which may be referred to as "intragranular voids" in this disclosure (see FIG. 1D). The average width of such pores (both inter- and intra-granular voids) may be in the range of from about 0.10 μm to about 5 μm, from about 0.10 μm to about 2 μm, or from about 0.20 μm to about 2 μm. As a measure of porosity, the total volume fraction of the pores in the Si-based materials may assume various values, e.g., from about 0.1% to about 5%, from about 0.1% to about 2%, or from about 0.5% to about 1% (for intragranular voids) and from about 20% to about 70%, from about 30% to about 60%, or from about 35% to about 55% (for intergranular voids). Pore dimensions and volume fraction may be determined using nano-computed tomography (nano-CT) from transmission X-ray microscopy (TXM) measurements as described in the Example, below.

Nanostructures within the Particles of the Si-Based Material

The particles themselves may be composed of an assembly of discrete, distinguishable nanostructures, the nanostructures having at least one dimension on the order of nanometers. The nanostructures may assume a variety of shapes. In embodiments, the nanostructures are elongated, having lengths which are greater than their diameters/widths. The term "nanowire" may be used in this disclosure to refer to such elongated nanostructures, but nanofibers, nanowhiskers, nanorods, etc., may also be used. The nanowires may have an average diameter/width in the range of from about 1 nm to about 50 nm, from about 1 nm to about 25 nm, from about 5 nm to about 20 nm, or from about 5 nm to about 10 nm, as determined from electron microscopy images according to the techniques described in the Example, below. The average length of the nanowires is not particularly limited, but is generally no greater than the length of the particle itself.

Within the assembly, the nanostructures, e.g., nanowires, may be assembled in the form of a regular, ordered array, although the particular arrangement of the nanowires within the array may vary. The array may be characterized by the alignment of the nanowires in the array. In embodiments, the nanowires are aligned along their longitudinal axes. In such embodiments, some neighboring nanowires may be arranged such that their longitudinal axes are substantially parallel (i.e., parallel although not necessarily perfectly parallel, e.g., within ±10° of being parallel) to one another while other neighboring nanowires may be arranged end-to-end such that their longitudinal axes run along the same axis. The array may also be characterized by the type of packing of the nanowires in the array (e.g., as visualized from transmission electron microscope (TEM) images and/or small angle X-ray scattering (SAXS) profiles). In embodiments, the array exhibits hexagonal packing. In other embodiments, the array exhibits gyroidal packing. Illustrative assemblies of arrays of nanowires are shown in FIGS. 1F and 1G.

Figure 2B:
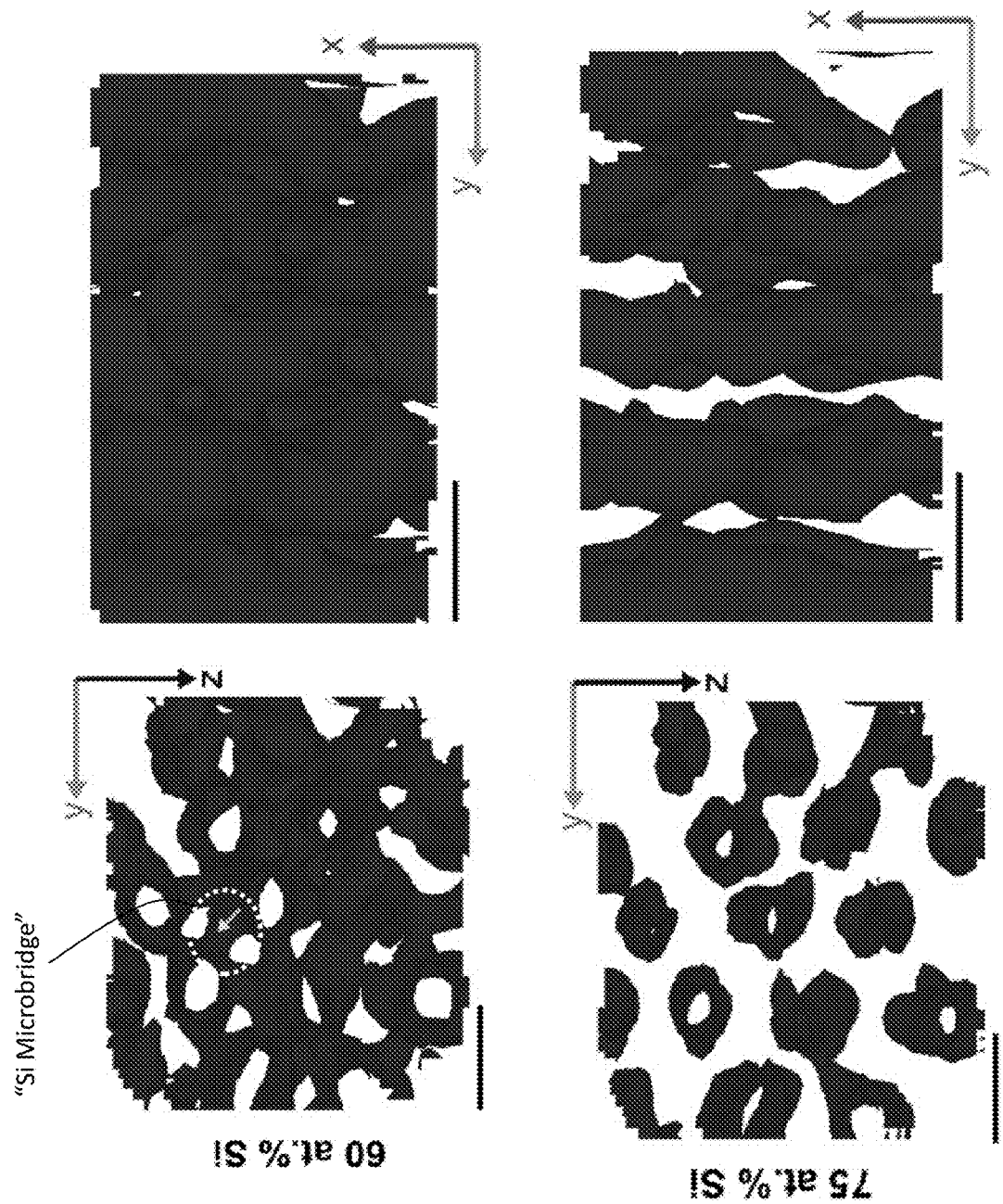

Within the assembly, at least some neighboring nanostructures, e.g., nanowires, may be directly connected to one another through bridges, each bridge extending from the surface of one nanowire to the surface of another nanowire. Neighboring nanowires may be connected by a plurality of bridges distributed along the lengths of each nanowire. Similarly, an individual nanowire may be connected to a plurality of neighboring nanowires via a plurality of respective bridges. Each bridge may be characterized by an angle, $\theta_b$, defined by the longitudinal axis of a nanowire from which the bridge extends and the longitudinal axis of the bridge. In embodiments, the average angle $\theta_b$ is in the range of from about 60° to about 90°, from about 70° to about 90°, or from about 80° to about 90°. In embodiments, the bridges are substantially orthogonal (i.e., $\theta_b$ is about 90°, e.g., within ±5% of 90°) to the nanowires to which each bridge connects. The lengths of the bridges are related to the inter-nanowire spacing. In embodiments, the bridges are nanometer-sized having each of their dimensions on the order of nanometers. The average length of the bridges may be in the range of from about 1 nm to about 10 nm, or from about 1 nm to about 5 nm, or about 2 nm. The average diameter/width of the bridges may be within similar ranges. Generally, the average diameter/width of the bridges is smaller than the average diameter/width of the nanostructures. Illustrative bridges within nanowire arrays are shown in FIGS. 1A, 2B and 2F. The angles $\theta_b$ and the dimensions of the bridges may be determined using atom-probe tomography (APT) as described in the Example, below.

Depending upon the particular configuration of the assembly of nanostructures making up the particles, the surfaces of the nanostructures can define a plurality of additional pores in the Si-based materials, the additional pores having shapes and sizes which are defined by the spacing between adjacent nanostructures as well as the configuration of their associated bridges. By way of illustration, the nanowire arrays shown in FIGS. 1A and 1G define a plurality of elongated, channel-like pores having average diameter on the order of a few nanometers, the pores distributed throughout the assembly of nanostructures, and thus, the particles of the Si-based material. As a measure of porosity, the total volume fraction of the all the pores in the Si-based materials may assume various values, e.g., at least about 20%, at least about 40%, at least about 60%, at least about 80%, at least about 90%, or in the range from about 20% to about 90%.

Although the Si-based materials are composed primarily of silicon, they can include measurable amounts of other elements. In embodiments, the Si-based materials include oxygen. The oxygen may form bonds with silicon such that the oxygen (and some of the silicon) is in the form of an oxide, $SiO_x$.

The Si-based materials may be characterized by a heterogeneous distribution of oxygen throughout the material. Both the chemical composition of the Si-based materials and the distribution of chemicals may be determined using APT as described in the Example, below. In embodiments, the nanostructures may include a smaller amount of oxygen as compared to the bridges. The average amount of silicon in the nanostructures may be at least 70 atomic %, at least 80 atomic %, or at least 90 atomic %. This includes embodiments in which the average amount of silicon in the nanostructures is in the range of from about 70 atomic % to about 95 atomic %, from about 80 atomic % to about 95 atomic %, or from about 85 atomic % to about 95 atomic %. (In such embodiments, the balance may be made up of oxygen.) In embodiments, the average amount of silicon in the bridges may be less than about 75 atomic %, less than about 65 atomic %, or less than about 55 atomic %. This includes embodiments in which the average amount of silicon in the bridges is in the range of from about 40 atomic % to about 75 atomic %, from about 40 atomic % to about 65 atomic %, or from about 45 atomic % to about 55 atomic %. (In such embodiments, the balance may be made up of silicon.) In embodiments, the oxygen which is present may reside at or near the surface of the nanostructure and/or bridge. The chemical heterogeneity of the Si-based materials is illustrated in FIGS. 2D-2F.

In embodiments, the Si-based materials are substantially free of any other elements besides Si and O. The term "substantially" is meant to indicate that such other elements are absent although the amount of such other elements may not be perfectly zero. However, the amount is so low that the Si-based materials would be considered to be composed of only Si and O such that their properties determined by Si and O. In embodiments, the Si-based materials are substantially free of Mg. The Si-based materials and the nanostructures of the materials may be characterized as consisting essentially of Si and O.

The term "average" used in this disclosure with respect to a particular structure, e.g., particles, nanostructures, bridges, etc., can refer to the average value obtained from a representative population of such structures.

The term "mesoporous silicon" may be used in this disclosure to refer to the Si-based materials.

Figure 3A:
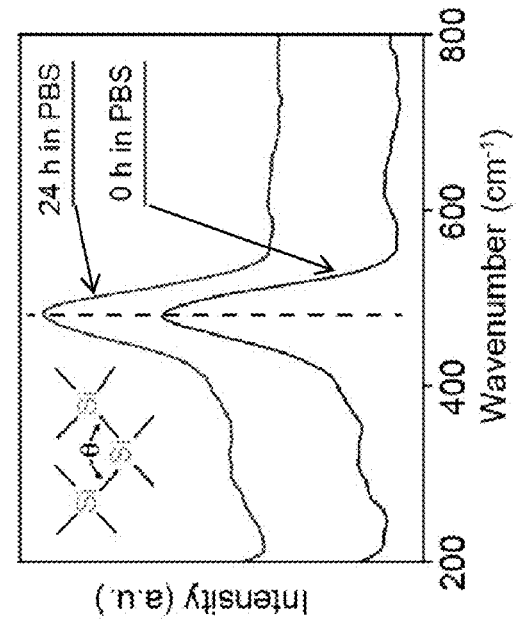
FIGS. 3A-3E illustrate that mesostructured Si provides less invasive biointerfaces.

The Si-based materials may be characterized by a number of properties. Regarding mechanical properties, the Si-based materials may be characterized by a Young's modulus, which provides a measure of the deformability of the Si-based materials. (See FIG. 3A.) In embodiments, the Young's modulus is no more than about 10 GPa, no more than about 5 GPa, or no more than about 2 GPa. This includes embodiments in which the Young's modulus is in the range of from 0.1 GPa to about 20 GPa, or about 0.1 GPa to about 5 GPa. These values may be average values, based on a number of samples of Si-based materials. These values may refer to the Young's modulus of the Si-based material in a dry state or after immersion in a buffer solution for about 2 hours as measured using the techniques described in the Example, below. However, the Young's modulus of the Si-based material after immersion is typically smaller than that of the Si-based material in the dry state. These values are significantly smaller than the comparative Young's moduli of dry bulk Si (about 180 GPa) and dry, electrochemically etched porous Si (about 20 GPa).

As further described in the Example, below, the Si-based materials are also biocompatible, biodegradable, electrically conductive, and exhibit enhanced intrinsic light absorptivity and reduced thermal conductivity, e.g., as compared to bulk Si or other porous Si materials.

Figure 8B:
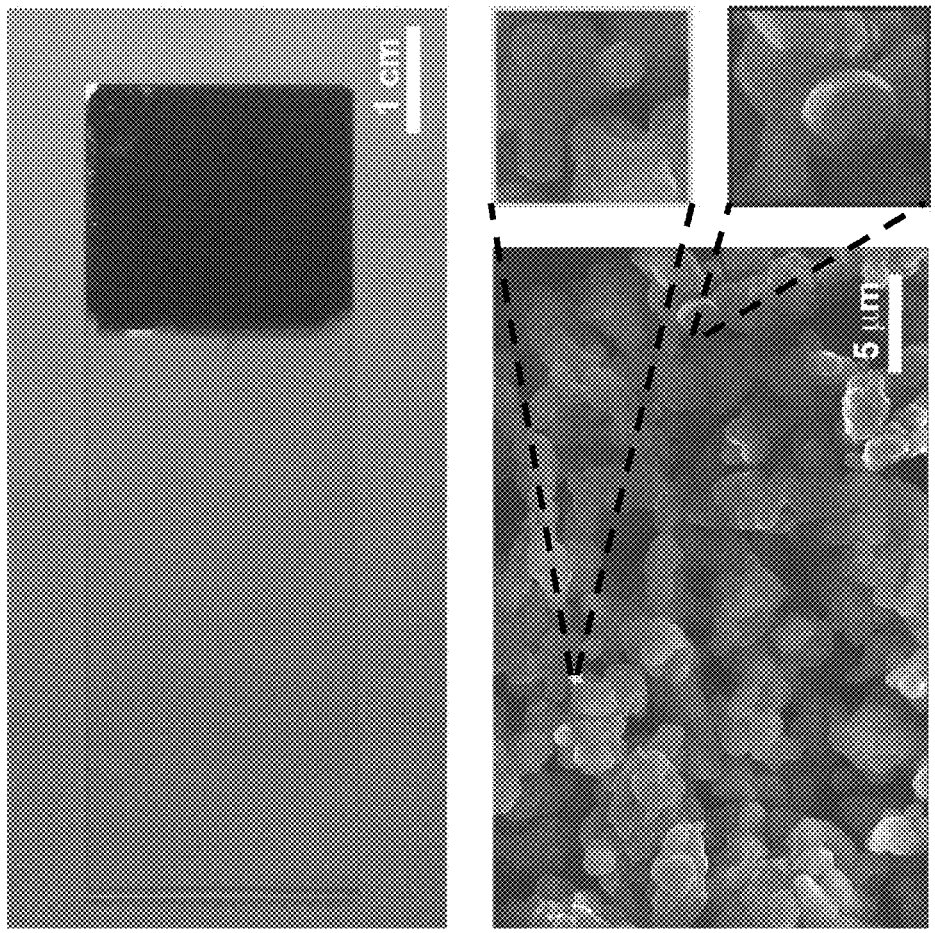
Figure 8A:
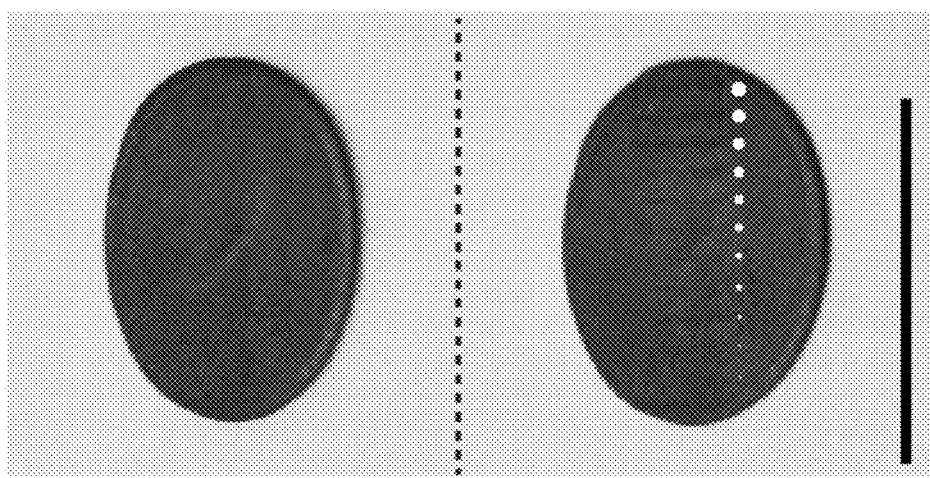

Depending upon the application, the Si-based materials may be used in a variety of forms. As further described in the Example, below, the Si-based materials may be a component of various compositions, e.g., a paste including the Si-based material and water; a suspension including the Si-based material and a suitable solvent such as water or alcohol; a gel including the Si-based material embedded therein. The Si-based materials may be in the form of a layer or film, e.g., formed by casting onto a desired substrate such as a polymer substrate. Such layers/films may be continuous or patterned. Illustrative such compositions and forms are shown in FIGS. 8A-8C.

The present disclosure also encompasses single particles of the Si-based materials as well as a plurality of such particles (e.g., in an aggregate).

Methods of Making the Si-Based Materials

As noted above, the methods of making the Si-based materials involve the use of a mesoporous silica ($SiO_2$) template. Mesoporous silica templates having a variety of particle shapes and pore shapes/dimensions/arrangements may be used. The mesoporous silica templates may be characterized as having uniform and ordered pore sizes in the range of from about 2 nm to about 50 nm. Illustrative mesoporous silica templates include hexagonal mesoporous silica, e.g., SBA-15, gyroidal mesoporous silica, e.g., KIT-6. Such forms of mesoporous silica templates are either commercially available or may be made using known methods (see "Methods II" in the Example, below). In addition, the particle morphology of SBA-15 may be adjusted (e.g., to form wheat-like particles, rods or spheres) by adjusting the conditions under which the SBA-15 is made (see "Methods II").

Figure 9A:
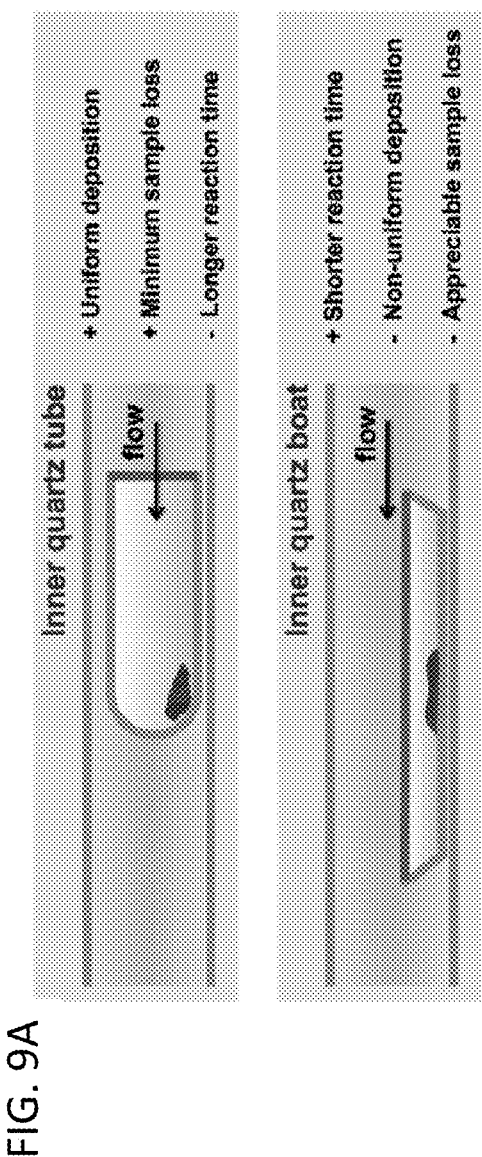
FIGS. 9A-9B show how the deposition system affects the morphology of mesostructured Si.
Figure 9B:
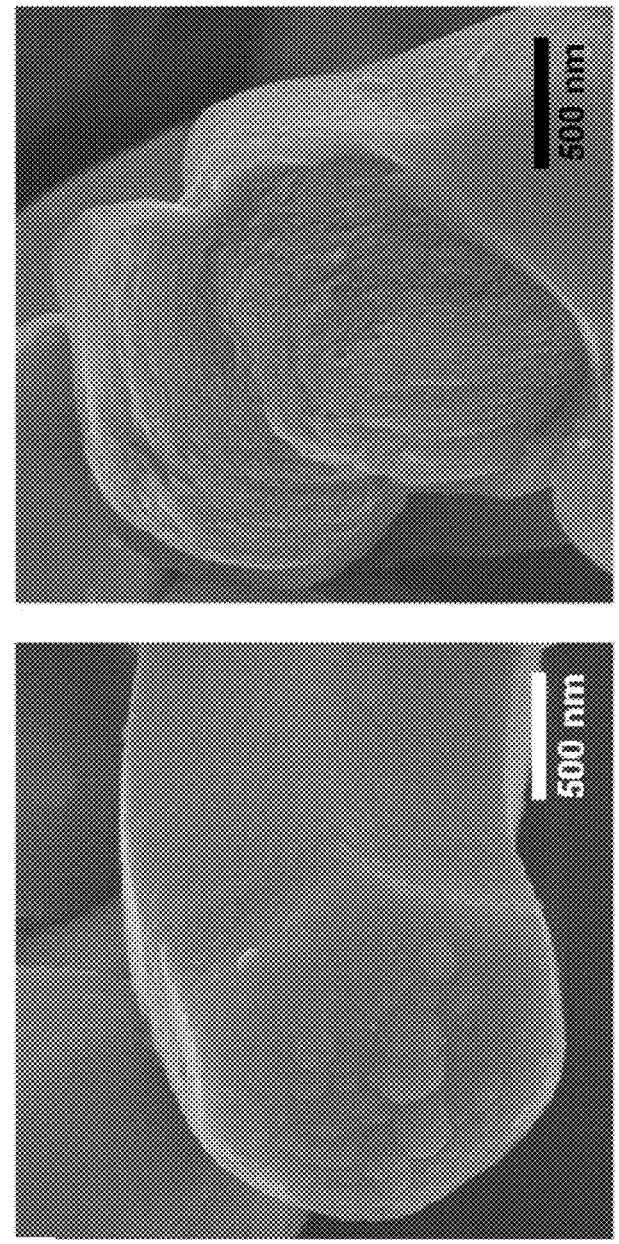

In embodiments, the method includes exposing the mesoporous silica template to a silicon precursor under conditions sufficient to deposit silicon on the surfaces of the mesoporous silica template via chemical vapor deposition (CVD). A variety of silicon precursors may be used, e.g., silane ($SiH_4$) and disilane ($Si_2H_6$). The term "conditions" refers to the conditions used during CVD, e.g., the growth temperature and the growth time. The growth temperature and growth time may be selected to optimize the uniformity of the nanostructure assembly and to maximize the product yield. The deposition can be carried out on a variety of CVD systems. In embodiments, the CVD system includes a double-tube deposition chamber. FIGS. 9A-9B demonstrate how the type of deposition chamber affects the morphology of the resulting Si-based material. (See also, FIG. 1B.) During CVD, the silicon precursor decomposes to silicon on the surfaces of the mesoporous silica template.

In a subsequent step, the method further includes removing the mesoporous silica template. Various techniques may be used to remove the mesoporous silica template, including etching, e.g., wet chemical etching. Illustrative conditions for carrying out the method are provided in the Example, below.

The method may include additional steps. By way of illustration, the Si-based materials can be filtered in order to select particles having a desired size/distribution of sizes.

The methods are distinguished from conventional methods of forming porous silicon. Electrochemical etching, for example, generally results in crystalline Si. Even if such methods could be adjusted to produce partially amorphous Si, the electrochemical process results in structures which differ from the disclosed Si-based materials (e.g., lack of bridges). Direct reduction of mesoporous silica also results in a different structure and chemistry since the mesoporous silica itself is directly transformed (i.e., rather than used as a template) and since chemical additives must be used.

Methods of Using the Si-Based Materials

The Si-based materials may be used in a variety of applications. Such applications include biological applications which exploit the optical and thermal properties of the Si-based materials. In embodiments, a method includes positioning the Si-based material in the vicinity of (e.g., in direct contact with) a lipid bilayer and illuminating the Si-based material with light sufficient to produce a photothermal response in the Si-based material. The lipid bilayer may be an artificial lipid bilayer or a natural lipid bilayer. The lipid bilayer may be part of a cell. The cell may be an excitable cell, e.g., a neuron, a muscle cell, etc. As further described in the Example, below, the illumination of light results in local, transient heating of the lipid bilayer via the photothermal effect. The local, transient heating induces a capacitance increase in the lipid bilayer which ultimately, can trigger an action potential. Thus, excitable cells may be activated by the Si-based materials. Illustration of this application is shown in FIGS. 4A-4G.

Light having various wavelengths may be used. The light may be selected to achieve a desired absorption by the Si-based material, e.g., light having a wavelength within the visible region of the electromagnetic spectrum. The power of the light may be selected to provide a desired local temperature/capacitance increase. The light may be pulsed (i.e., as opposed to continuous), e.g., to trigger a series of action potentials, i.e., a spike train. Various light sources may be used, e.g., lamps, lasers, fiber optics, etc.

Because the Si-based materials are porous, biocompatible and biodegradable, they may also be used in delivery applications in which drugs and/or other compounds are embedded into the Si-based materials for delivery to a desired subject.

These and other applications mean that the Si-based materials may be used in various methods of treating subjects, e.g., mammalian subjects, in which the Si-based materials are introduced or administered to such subjects. By way of illustration, oral or intravenous administration may be useful for drug delivery applications. Subcutaneous delivery may be useful for activating muscle cells.

Further details and experimental data relating to the Si-based materials and methods may be found in U.S. provisional patent application No. 62/350,328, the entire contents of which are hereby incorporated by reference.

Example

Introduction

Silicon-based materials have widespread application as biophysical tools and biomedical devices, however the fundamental forms are few. Provided is a biocompatible and degradable mesostructured silicon with multiscale structural and chemical heterogeneities. The material was synthesized using mesoporous silica as a template through a chemical vapor deposition process. It has an amorphous atomic structure, an ordered nanowire-based framework, and random sub-micron-scale voids. The material shows an average Young's modulus that is 2-3 orders of magnitude smaller than that of single crystalline silicon. Additionally, a remotely-controlled, temporally transient and lipid bilayer-supported bioelectric interface was designed that permits non-genetic and sub-cellular optical modulation of the electrophysiology dynamics in single dorsal root ganglia neurons, resulting in an unusual type of hybrid cellular system. The results show that biomimetic expansion of silicon into heterogeneous and deformable forms will open up new opportunities in extracellular biomaterials or bioelectric systems.

Methods

Synthesis of Mesostructured Si.

Mesostructured Si was prepared by CVD of Si inside mesoporous $SiO_2$, followed by HF etching to remove the template. Si was deposited at 500° C. and 40 Torr using silane as the Si precursor and hydrogen as the carrier gas. In a typical synthesis, 200 mg of $SiO_2$ template was used, with flow rates of $H_2$ and $SiH_4$ set at 60 and 2 standard cubic centimeters per minute, and a total CVD duration of 120 min. Subsequent HF etching for 5-10 min was used to remove the template at room temperature.

Structural Characterizations.

SAXS measurements were conducted at the 12ID-B station at the Advanced Photon Source (APS), Argonne National Laboratory (ANL). TXM nano-CT was performed on the new transmission X-ray microscope at sector 32-ID of APS in ANL. SEM was performed on a Merlin FE-SEM (Carl Zeiss, Germany). TEM and SAED were done using a Tecnai F30 TEM (FEI, USA).

Atom-Probe Tomography (APT).

The APT was run in an ultraviolet (UV) laser-assisted local-electrode atom-probe (Cameca, USA, LEAP 400XSi). Surface atoms from a microtip were evaporated with an applied voltage of 1~6 kV and the assistance of a 30 pJ UV (wavelength $\lambda$=355 nm) laser pulsing at 250 kHz frequency. The samples were held at 30 K and $2 \times 10^{-11}$ Torr during APT experiments. The 3D reconstructions and data analyses were performed using Cameca's Integrated Visualization and Analysis Software (IVAS) 3.4 code.

Atomic Force Microscopy (AFM) Measurements.

Force curves were collected using an Asylum MFP-3D AFM (Asylum Research, USA) with ACTA (AppNano, USA, nominal spring constant 40 N/m) probes in air and AC240 (Olympus, Japan, nominal spring constant 2 N/m)

probes in liquid. Prior to solution phase AFM experiments, samples were also soaked in 1×PBS solution at room temperature for ~2 h. Force curves were recorded by loading at a rate of 1 μm/s up to an indentation depth of ~10 nm, followed by unloading at the same rate.

UV-Vis and Raman Spectroscopy.

Diffuse reflectance UV-Vis spectra were collected on a Cary 5000 UV-Vis-NIR spectrometer (Varian, USA) equipped with a diffuse reflectance accessory (DRA). Raman spectra were recorded using a LabRAM HR evolution system (Horiba, Japan).

Cell/Si Interfaces Imaging.

HUVEC/Si mixtures were either frozen under high pressure and freeze-substituted or chemically fixed before epoxy resin embedding. Epoxy sections of ~100 nm were cut using an ultramicrotome and collected on copper grids for imaging on a Tecnai F30 TEM (FEI, USA).

Calcium Imaging.

HUVECs were stained with Fura-2 AM and washed with a HEPES-buffered Tyrode's solution. Mesostructured and solid Si particles have similar lateral sizes of ~5 μm. Particles sitting on cell bodies were pushed by glass micropipettes controlled by a micromanipulator. After making contact with the particles, pipettes were lowered by another 1 μm and held still for 20 s before retraction. During the whole process, fluorescence images were collected using an upright microscope (BX61WI, Olympus, Japan) equipped with an EM-CCD camera (C9100-13, Hamamatsu Photonics, Japan).

Artificial Lipid Bilayer Experiments.

A custom-made upper chamber containing a 300 μm diameter hole for planar lipid bilayer (asolectin lipids, soybean polar lipid extract, Avanti Polar Lipids, USA) formation was used and placed in a glass-bottomed lower chamber. Mesostructured Si particles were applied into the upper bath solution and allowed to settle down to form contact with the bilayer. Laser pulses (532 nm) were delivered through a 10×/0.25 NA lens and the power was adjusted by a set of neutral density filters manually. The laser pulse frequency and duration were controlled by the in-house software and external custom-made hardware. For the capacitance measurements, the current responses of the bilayer were recorded when a 5 kHz sinusoidal carrier voltage signal was concurrently used as the voltage command, while Si-based film was illuminated by the laser pulses. For the local temperature measurements, a pipette electrode (2~4 MΩ) filled with bilayer bath solution was placed adjacent to the stimulation site. Capacitive currents were recorded in voltage-clamp mode. A laser pulse was delivered to the preparation 300 ms after the voltage was jumped from a holding potential of 0 mV to the desired voltage.

DRG Neurons Experiments.

DRGs were extracted from P1-P3 Sprague-Dawley rats and cultured following existing protocols (See Methods II, below). Mesostructured Si particles were delivered and settled onto DRG cultures. Targeted neurons with a single particle attached to the soma were patched using a ~2 MΩ pipette. Voltage recordings were made in current clamp mode. Every three seconds, a 1 ms suprathreshold amplitude current injection was delivered to the neuron to assess its excitability and followed by a 1 ms laser pulse through a 40×/0.55 NA lens, 300 ms later. The minimal power enough to elicit APs was determined and applied in trains of laser pulses at different frequencies.

Results and Discussion

This Example demonstrates the synthesis of three-dimensional (3D) Si-based biomaterials with an ordered and uni-directionally aligned fibril-based framework (FIG. 1A, bottom). This framework is fundamental to many natural biomaterials[16,23] (e.g., bone[16]) and extracellular matrices (ECM)[24] (See also, FIG. 1A, top). A nano-casting approach[17,25-28] was applied with ordered hexagonal mesoporous silica ($SiO_2$) SBA-15[29] as the template, in which silane ($SiH_4$) decomposition inside the channels and pores provided the nanowire arrays with self-supporting microbridges[25,26]. A chemical vapor deposition (CVD) apparatus was designed with a double-quartz-tubing system (FIG. 9A) in which the $SiO_2$ template (SBA-15) was placed near the bottom of the inner tube (FIG. 1B). An optimal (uniform morphology, maximum yield) growth temperature of 500° C. with a duration of 2 h was identified, when 200 mg of SBA-15 template was used. After CVD, subsequent wet chemical etching with hydrofluoric acid (HF) removed the $SiO_2$ and yielded a brownish powder (FIG. 1B). The scanning electron microscopy (SEM) image shows wheat-like aggregates with individual grain width of ~2 μm (FIG. 1C). The size or morphology uniformity can be adjusted by using shape-controlled SBA-15 templates (e.g., rod-like or spherical shapes, FIGS. 5A and 7A), or adopting post-synthesis separations (e.g., filtering to obtain a desired shape distribution). The freshly etched and dried Si-based samples did not result in combustion upon xenon flash illumination or mechanical grinding, suggesting that the mesostructured Si surfaces are ignition-resistant in air[1]. The sample is electrically conductive, and single particle measurements yielded a representative electrical conductance of 2.4 μS (data not shown). The powder can be molded and embossed like clay (FIG. 8A), dispersed as a suspension and drop-casted to form thin films (FIG. 8B), and injected and retained locally within collagen hydrogel (FIG. 8C).

Nano-computed tomography (nano-CT) from transmission X-ray microscopy (TXM) measurement reveals that individual particle aggregate contains random micron- and sub-micron scale inter- or intra- (blue) granular voids (FIG. 1D), reminiscent of the cavities in spongy bones. The voids have a total volume fraction of 0.7% (intra-)/50.0% (inter-) and width of ~0.2-2 μm (data not shown), likely formed through the diffusion-limited incomplete filling of Si inside mesoporous $SiO_2$.

A small angle X-ray scattering (SAXS) profile (FIG. 1E) exhibits diffraction peaks indexed as (100), (110) and (200) of a two-dimensional hexagonal structure (space group, p6mm), as expected from the SBA-15 template[29]. The lattice constant a calculated from SAXS was 11.1 nm, which is consistent with that of the $SiO_2$ template (11.0 nm) and suggests a faithful replication. The Brunauer-Emmett-Teller (BET) specific surface area and total pore volume as measured by $N_2$ sorption were 462 $m^2/g$ and 0.53 $cm^3/g$, respectively (data not shown).

The high-resolution SEM shows assemblies of aligned nanowires within individual grains (FIG. 1F), as expected from the channel structures in SBA-15 template. The end-view transmission electron microscopy (TEM) image and the fast Fourier transform (FFT) diffractogram (FIG. 1G) confirm the hexagonally ordered packing of nanowires. Selected area electron diffraction (SAED) shows diffuse rings and indicates that Si is amorphous (FIG. 1G), a useful property for improving light absorption[31] and reducing rigidity[32] in Si. In-situ heating experiments with both TEM and SAXS showed that the ordered mesostructures remained at 900° C. for at least 2 hours, although partial crystallization was observed (data not shown). Finally, this synthetic approach is generalizable to other Si frameworks, e.g., a gyroidal lattice with a space group of Ia$\bar{3}$d (data not shown).

The high-angle annular dark-field scanning transmission electron microscopy (HAADF STEM) image highlights individual nanowires (data not shown), whose ordered packing suggests the existence of interconnecting micro-bridges[25,26]. Energy dispersive X-ray (EDX) mapping of one representative area shows an alternating distribution of oxygen (O) and Si (data not shown). Because a long etching time (5-10 min in HF) was adopted to remove the $SiO_2$ template, and given the large pore volume (i.e., 0.53 $cm^3/g$) exhibited by the material, the O signals came primarily from the oxidized portions in the Si open framework instead of from the $SiO_2$ template residuals.

To quantitatively determine the heterogeneous O distribution, atom probe tomography (APT) was used to obtain elemental distributions in a Si framework with sub-nanometer scale spatial resolution (FIGS. 2A-2F). A reconstructed 3D dataset (FIG. 2A), collected from one Si particle with an intact $SiO_2$ template (i.e., without dissolving $SiO_2$ by HF), displayed a hexagonal arrangement of nanowires with a lattice constant of 10.7 nm, consistent with the SAXS and TEM results (FIG. 1G). Additionally, individual micro-bridges can be readily visualized (FIG. 2B, arrow), and statistical analyses (n=34) demonstrated that the angles between a micro-bridge and its adjacent nanowires peaked at ~90° (data not shown). Given this quasi-orthogonal arrangement between nanowires and micro-bridges, it was possible to isolate two components in orthogonal thin slices (FIG. 2C).

Next, the distribution of Si and O atoms was studied using isoconcentration surface analysis (FIG. 2B). The results demonstrate that although the interconnecting micro-bridges are visible in the 60 at. % Si isoconcentration surface map (FIG. 2B, upper panel), most of them no longer appear in the 75 at. % one (FIG. 2B, lower panel), indicating that the overall Si(O) concentration is less (more) in the micro-bridges. The proximity histogram concentration profile averaged over the selected region was further analyzed (FIG. 2D). Because the micro-bridges have smaller diameters than nanowires (i.e., <2 vs. ~7 nm), Si oxidation due to O incorporation from the $SiO_2$ template or air places the Si concentration generally below 75 at. % in micro-bridges (FIG. 2D, thick line). Moreover, this Si concentration difference can be quantified using a concentration distribution histogram derived from isoconcentration surface analysis within the two slices (FIG. 2E), which displays distinct distributions in each domain (<75 at. % for micro-bridges, <95 at. % for nanowires) (FIG. 2E). Finally, the Si concentration in the template (i.e., $SiO_2$ regions that are away from the $Si/SiO_2$ interface) was ~43 at. % (FIG. 2D), higher than that in pure $SiO_2$ (i.e., 33 at. %). This suggests that silane decomposition can also occur inside sub-nanometer cavities within the mesoporous $SiO_2$ walls, confirming a domain previously proposed as microporous 'corona'[33]. Taken together, the electron microscopy (FIGS. 1F, 1G), EDX (data not shown) and APT (FIGS. 2A-2F) demonstrate that the Si framework exhibits a chemical heterogeneity, where amorphous Si constitutes most of the nanowire-based component and the thinner micro-bridges have an overall higher O concentration and integrates the nanowires (FIG. 2F).

Next, the physical properties related to the observed structural and chemical heterogeneities were explored. Given their critical role in establishing minimally invasive biointerfaces[3,34,35], the mechanical properties were studied first. In a dry state, the Si framework showed an average Young's modulus of 1.84 GPa (FIG. 3A), which is ca. 2 and 1 orders of magnitude smaller than that for bulk Si (~180 GPa) and electrochemically etched porous Si with similar porosity (~20 GPa)[1], respectively. This significant reduction in modulus is likely a combined result of multi-scale porosity, an amorphous framework, the molecular-level feature sizes of both nanowires and the micro-bridges, and the chemical heterogeneity as identified by APT (FIGS. 2D, 2E).

Figure 3B:
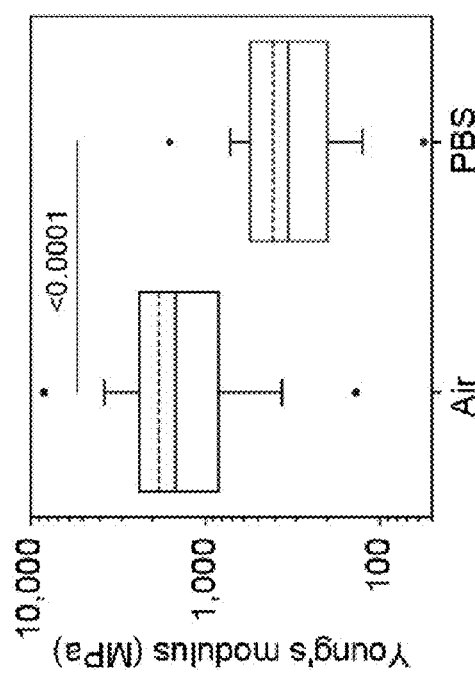
Figure 3C:
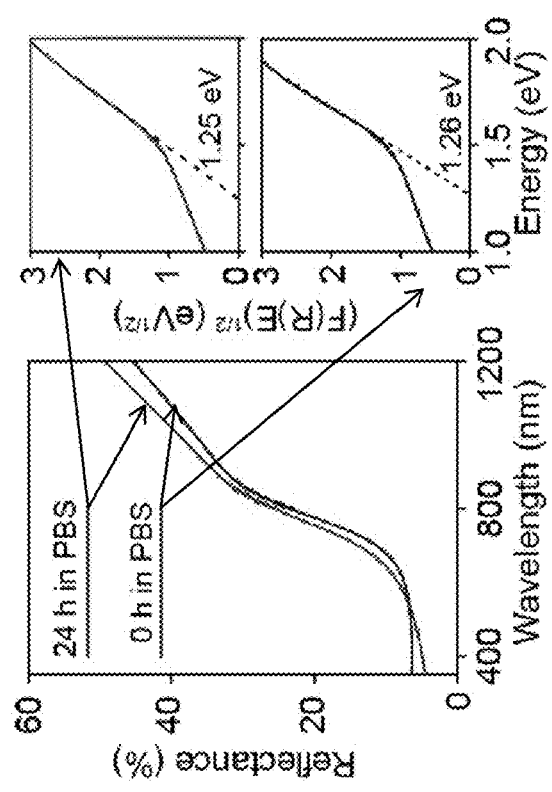

After being immersed in a phosphate-buffered saline (PBS) solution for ~2 hours, the average Si Young's modulus decreased to 0.41 GPa (FIG. 3A), comparable to that of hydrated collagen fibers[36] and only 1 order of magnitude larger than that of phospholipid bilayers[37]. This reduction of modulus may come from framework degradation in saline, especially through the O-rich micro-bridges that maintain the framework integrity. However, in-situ and ex-situ SAXS (data not shown) show that ordered mesostructures dominate in the remaining insoluble material for at least two days at room temperature in both PBS and collagen hydrogel. Cross-sectional TEM also shows long-range order in the interior of these saline treated samples (data not shown), although partially-degraded nanowire segments can be observed (data not shown). Raman and ultraviolet-visible (UV-vis) spectra indicate that the remaining Si materials displayed marginal changes in their atomic structures (i.e., the characteristic transverse optical Raman peak position and width, correlating with the spread in mean Si—Si—Si bond angle[38], remain at ~480 $cm^{-1}$ and ~59 $cm^{-1}$) and optical properties (e.g., the optical band gap) after being immersed in PBS for 1 day (FIGS. 3B, 3C). These results suggest that the interior of the Si mesostructures were preserved, and that the measured modulus reduction in saline is likely a result of degradation of particle surfaces. Indeed, surface accumulation of degradation products has been observed in a confined space, e.g., a cavity from a piece of wrapped human umbilical vein endothelial cell (HUVEC) membrane (data not shown). Overall, this degradation pathway is surface-initiated, instead of being bulk degraded (as usually expected for water-permeable nanoporous materials). This behavior is attributed to the possible blockage of molecular-level pores by the partially-degraded products (i.e. gel-like $Si_xO_y(OH)_z^{4x-2y-z}$) over particle surfaces (data not shown), which may delay the disruption of the internal ordered framework in saline—as seen in both SAXS and TEM (data not shown). Finally, mesostructured Si can completely degrade[10,11] in saline over time and its behavior is dependent on multiple factors, such as initial Si/water ratio, solution exchange protocol, and temperature (data not shown).

Figure 3D:
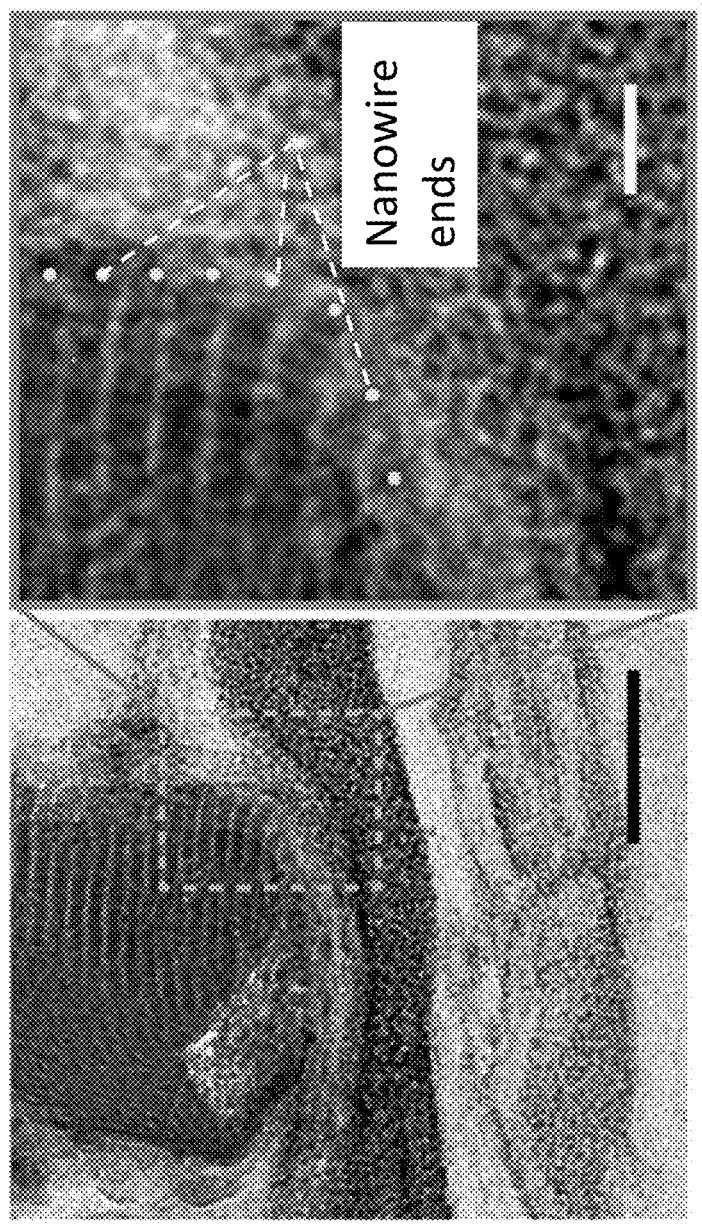

Close inspection at the Si/HUVEC interfaces reveals a minimum of ~30 nm wide space between the ordered domains of Si particle and the plasma membrane (FIG. 3D), likely filled with degraded Si that is more deformable (FIG. 3A) and natural ECM. Additionally, little correlation was observed between the nanowire orientation and the cell surfaces, as shown in samples prepared with both freeze-substitution (FIG. 3D) and chemical fixation (data not shown) methods, suggesting that nanoscale surface topography from Si particle may not be critical for establishing stable biointerfaces.

Figure 3E:
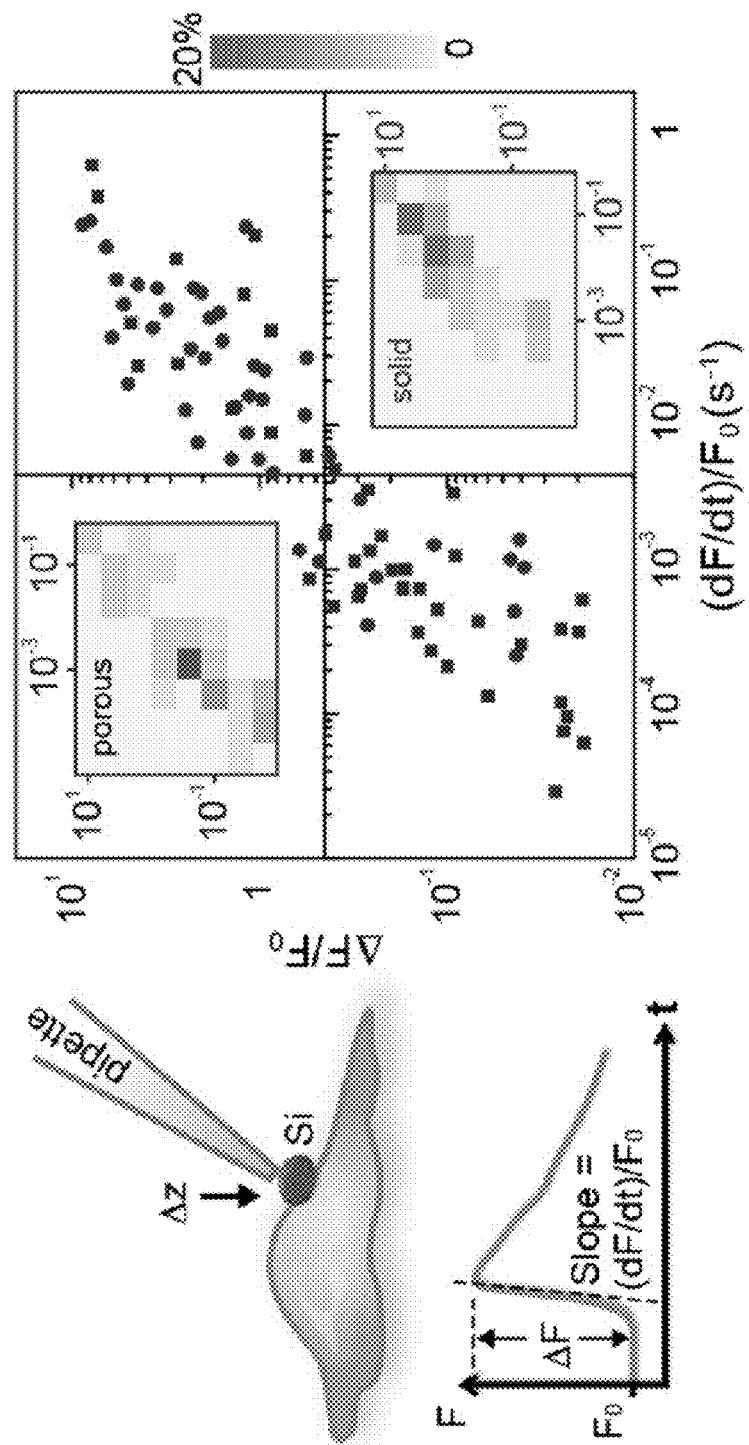

To evaluate the biological benefit of using mesostructured Si, a single cell calcium-imaging assay was developed in which fluorescence dynamics were recorded upon pressing vertically on a HUVEC cell-supported Si particle (size: ~5 µm) with a glass micropipette (FIG. 3E). Compared to grinded single crystalline Si particles, mesostructured Si yields statistically smaller values in both amplitude ($\Delta F/F_0$)

and slope (($dF/dt$)/$F_0$) in the mechanically-induced calcium dynamics curves (FIG. 3E). These single cell studies confirm that deformable materials are less invasive to cellular components[3]. Finally, mesostructured Si yielded negligible cytotoxicity in several mammalian cell cultures (data not shown). And when tested in rats subcutaneously, it only caused a minor inflammatory response, which decreased substantially from 1-day to 3-week time points as the material degraded (data not shown).

Figure 4A:
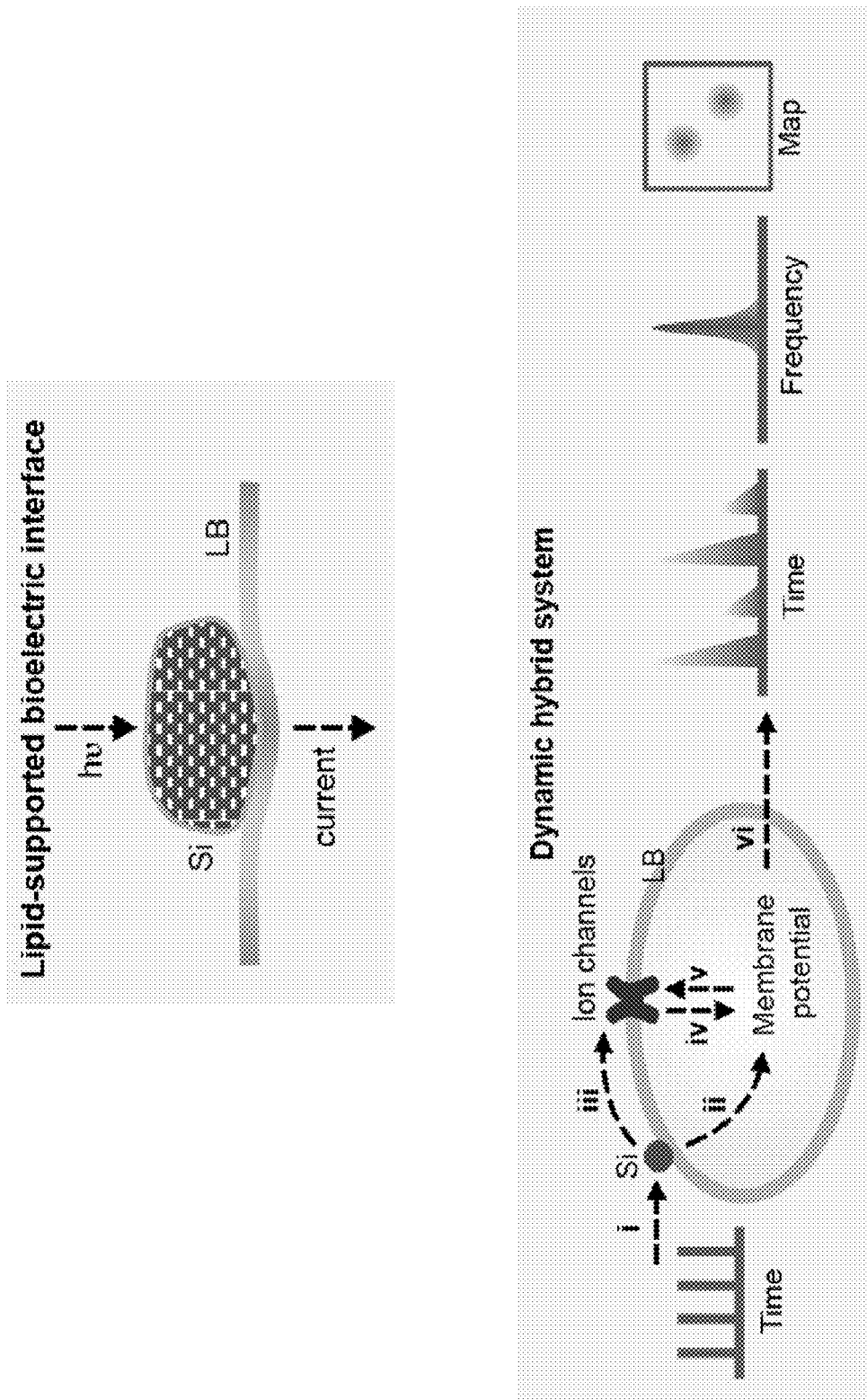

Altogether, this biocompatible and degradable form of Si has intrinsic (i.e., as grown) and induced (e.g., by water) chemical and structural heterogeneities, despite its origin from a single Si precursor (i.e., $SiH_4$). Given that these heterogeneities are spatially organized and seamlessly integrated, a single particle may exhibit multiple functions (data not shown), a scenario similar to that in natural biominerals[16,39]. For example, good photothermal efficacy is expected from the interior of the Si mesostructures due to enhanced intrinsic light absorptivity in amorphous Si[31], and reduced thermal conductivity and capacity as previously demonstrated for porous Si[1]. Taking advantage of the fact that a rapid temperature variation can induce transient capacitive currents in phospholipid bilayers[40,41], a hybrid Si/phospholipid system was constructed as a remotely controlled bioelectric interface (FIG. 4A, top). A layer of grinded Si mesostructures (individual particle size: ~1-2 μm) was supported over one side of a phospholipid bilayer, and its local junction with lipids was remotely actuated with 532 nm laser pulses (laser beam diameter: ~40 μm; FIG. 4B). The temperature change near the mesostructured Si layer was measured using a calibrated micropipette resistance method[40]; simultaneously, the electrical capacitance dynamics was assessed with the impedance method[40] using a sinusoidal voltage (FIG. 4B). Next, membrane current dynamics was recorded under voltage-clamp mode (FIG. 4B and details in "Methods II," below). Experiments and finite element analysis simulation revealed a fast photothermal effect (FIG. 4C, upper panel), and such a fast response is critical for capacitive current generation in lipid bilayer[40]. For example, one 11.2 μJ laser pulse causes a ~5.8 K increase of local temperature within 1.8 ms, followed by a decay to baseline with ~2.2 ms time constant (FIG. 4C, upper panel). With the same pulse, the estimated capacitance change accompanying the fast temperature rise peaks at ~0.6% (FIG. 4C, lower panel). Because impedance correlates inversely to capacitance, a fast increase in bilayer capacitance due to laser pulses leads to a reduction of impedance, and correspondingly, a light-induced transient membrane current. Such a membrane current is capacitive and depolarizing (i.e., current flow tends to reduce the polarization in the phospholipid bilayer); its amplitude is tunable with either laser input energy (data not shown) or a voltage drop across the bilayer (FIG. 4D). Because both the membrane current output and the local temperature variation are transient, this Si/bilayer platform may be adapted for minimally invasive and dynamic biomaterials or devices.

Figure 4F:
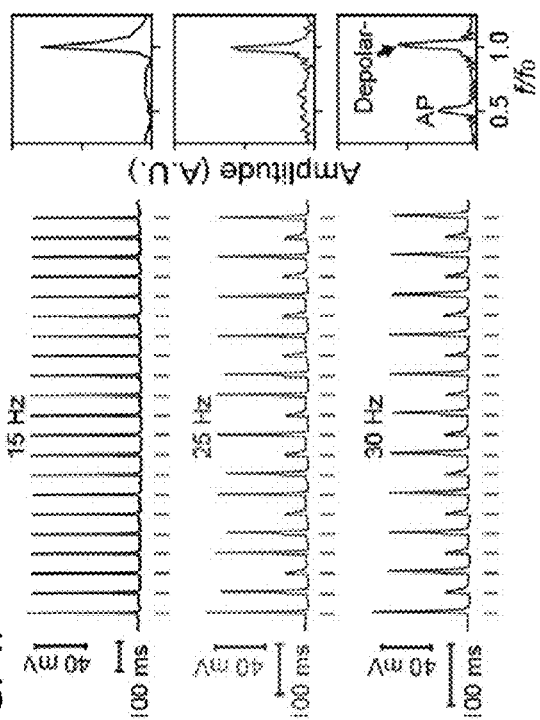
Figure 4G:
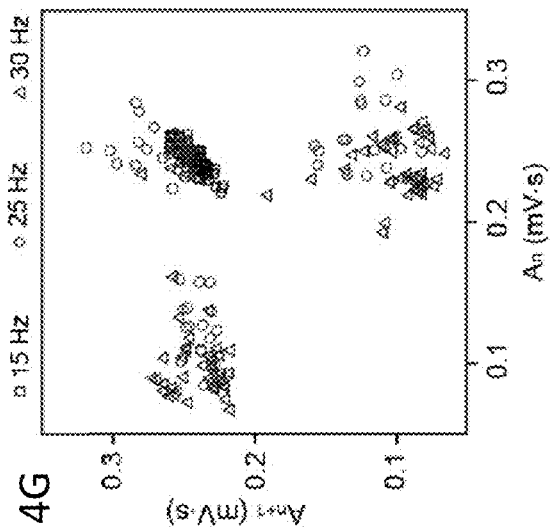
Figure 4E:
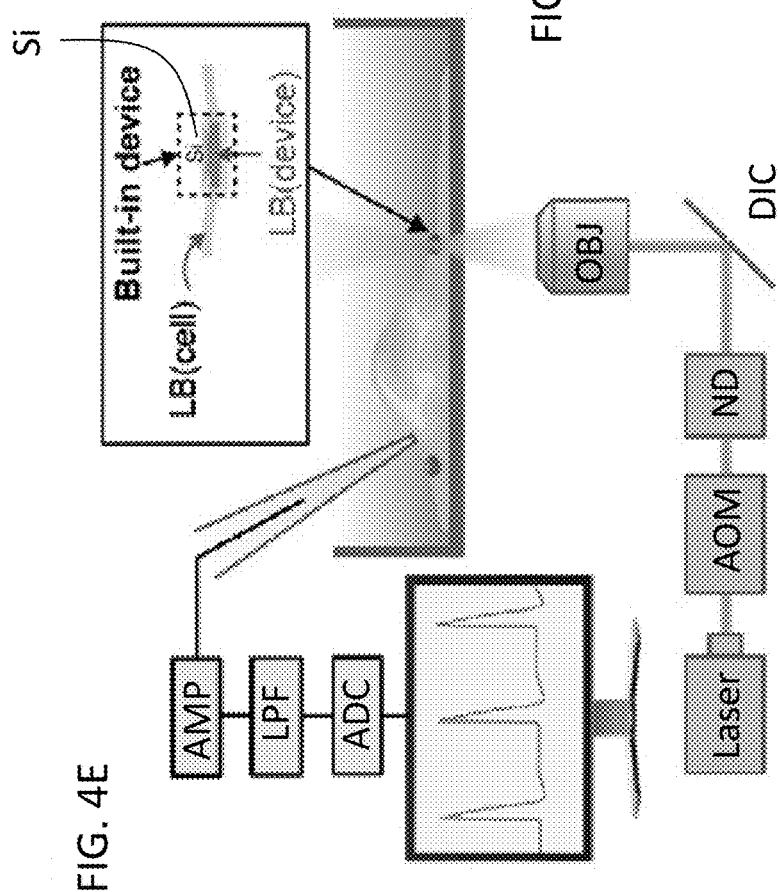

To investigate this possibility, a dynamic hybrid Si/cell system was developed (FIGS. 4A and 4E) where individual mesostructured Si particles attached to dorsal root ganglia (DRG) neurons, with 532 nm laser pulses and intracellular electrical recordings as input and output, respectively (see "Methods II," below). Individual micron-scale and thermally stable (data not shown) Si mesostructures are preferable over ensembles of existing nanoparticles[41] in order to achieve efficient and point-like localized extracellular control, as well as to avoid material internalization by neurons[42] or laser heating-induced particle change[43]. By varying the laser stimulation duration while fixing its wavelength and power (532 nm, 5.32 mW, beam diameter: ~10 μm), an average of 5.32 μJ threshold energy was identified for reliably eliciting single action potentials (AP) in DRG neurons with a singly attached Si particle (particle size: ~2 μm). This energy level is ~30× less than those used for a recently reported precise neuromodulation with Au nanoparticles[41]. Given the experiments on phospholipid bilayers (FIGS. 4B, 4C and 4D) and the controls with mesoporous $SiO_2$ (data not shown), under current-clamp conditions, the fast and transient photothermal effect from the Si framework (data not shown) induces depolarization that opens sodium channels thus triggering APs. Since neurons process information via spike trains, this process was mimicked by delivering trains of 5.32 μJ laser pulses with different frequencies. Reproducible and precise optical stimulation up to 15 Hz was demonstrated (FIG. 4F, upper). At higher frequencies, AP generation becomes less efficient, although a deterministic sub-threshold depolarization remains evident (data not shown). After reaching 20 Hz, e.g., at 25 Hz (FIG. 4F, middle), the neural stimulation efficacy declined, response time (spike latency) and its standard deviations (trial-to-trial jitter and throughout train jitter) increased (data not shown), all of which are most likely limited by the intrinsic ion channel kinetics (FIG. 4A, bottom)[40,44]. Interestingly, at 30 Hz input, the real-time electrical recording trace shows a quasi-alternating pattern of APs and sub-threshold depolarization (FIG. 4F, lower). Accordingly, fast Fourier transform of the time-dependent trace shows a splitting distribution in the frequency domain (FIG. 4F lower right panel), one at half-input frequency (for APs) and the other at the original input frequency (for sub-threshold depolarization). This emergent output behavior results from dynamic feedback[44] among Si-induced thermal and ionic effects, ion channel activities and membrane potentials (FIG. 4A, bottom). A return map analysis (FIG. 4G, $A_n$-$A_{n+1}$, $A_n$ is the area of the $n^{th}$ induced neuronal signal)[44] shows frequency dependent 2-D patterns, being either focused (e.g., 15 Hz) or partitioned/diffused (e.g., 30 Hz), suggesting another mechanism for output recognition.

Systematic control of the position and efficacy of Si/cell interfaces and demonstration of more complex dynamic behaviors in the hybrid system is possible since individual mesostructured Si particles can be positioned in an arbitrary manner by a glass micropipette (data not shown), that Si particles can be patterned as a micro-pad array over centimeter-scale area by photolithography (data not shown), and that size- and shape-controlled preparation of Si particles is achievable as described above. Additionally, tools such as light-emitting diode and calcium imaging can be explored for stimulation and recording of neural activities, which would be beneficial for in vivo studies.

Existing materials, such as particles of single crystalline silicon or carbon, may be configured into similar interfaces, although they do not currently exhibit the deformability or degradability desired for biomaterials. Hydrogels and polymers[45,46] are softer and may form mechanically compliant interfaces for similar studies, however appropriate chemical designs are needed for achieving both degradability and fast photothermal dynamics (e.g., a few degrees of temperature increase within milliseconds). Regardless of exploring other materials, the current demonstrations of lipid bilayer-level integration of a bioelectric interface and the hybrid cellular system show that amorphous Si, a much less exploited material in biomedical research, may be used as a building block in establishing functional bio-interfaces[13,35,47-49] and as a new bio-orthogonal and dynamic component for future synthetic biology[50].

Methods II

This section provides additional detail for the Methods described above.

Synthesis of Mesostructured Silicon (Si).

Mesostructured Si materials were prepared by chemical vapor deposition (CVD) of Si inside mesoporous silica ($SiO_2$), followed by hydrofluoric acid (HF) etching to remove the template. Four types of mesoporous silica templates were adopted for the synthesis of mesostructured Si, including wheat-like SBA-15, rod-like SBA-15, sphere-like SBA-15, and KIT-6. Mesostructured Si synthesized from wheat-like SBA-15 was used for all the characterizations and applications shown in the figures.

Wheat-like mesoporous silica SBA-15 was synthesized according to a previous report[1]. Briefly, Pluronic P123 (Sigma-Aldrich, USA) was dissolved in a hydrochloric acid (HCl) (Sigma-Aldrich, USA) solution. Next, tetraethyl orthosilicate (TEOS) (Sigma-Aldrich, USA) was added and the mixture was stirred at 35° C. for 24 h. The chemical composition of the reaction mixture was 4 g P123: 0.04 mol TEOS: 0.24 mol HCl: 6.67 mol $H_2O$. The mixture was then aged hydrothermally at 100° C. Finally, the powders were filtered, dried and calcined at 500° C. for 6 h.

Rod-like SBA-15 was synthesized following a previous report[2]. 4.0 g of P123 was first dissolved in a mixture of 30 g of deionized (DI) water and 120 g of 2 M hydrochloric acid (HCl) by stirring at 35° C. overnight. 8.5 g of TEOS was then added to the aqueous solution under vigorous stirring. The mixture was stirred for 5 min before being kept under static condition at 35° C. for 20 h. The product was aged at 100° C. for another 24 h. After filtering and washing with water, the final product was dried and calcined at 550° C. for 6 h.

Sphere-like SBA-15 template was made based on a previous report using cetyltrimethylammonium bromide (CTAB) as a co-surfactant and ethanol (EtOH) as a co-solvent[3]. In a typical synthesis, 3.0 g of P123 was dissolved in 60 mL of 1.5 M HCl while 0.6 g CTAB (Sigma-Aldrich, USA) was mixed with a separate 25 mL of water. After both surfactants have been dissolved, two solutions were mixed together and 20 mL of 100% EtOH (Thermo-Fisher Scientific, USA) was added to the mixture. 10 mL of TEOS was then added dropwise to the above mixture solution of surfactants under vigorous stirring (~500 rpm). After stirring at 35° C. for 45 min, the mixture was kept static under 75° C. for 10 h and aged at 100° C. for another 24 h. The product was filtered, washed, dried and calcined at 550° C. for 6 h.

The synthesis of KIT-6 template followed a previous report using n-butanol (BuOH) as a co-solvent[4]. 6 g of P123 was dissolved in 217 g of DI water and 11.8 g of concentrated HCl (37%). 6 g of BuOH (Sigma-Aldrich, USA) was added under stirring at 35° C. After 1 h stirring, 12.9 g of TEOS was added at 35° C. to make the molar ratio as TEOS:P123:HCl:$H_2O$:BuOH=1:0.017:1.83:195:1.31. The mixture was left under stirring for 24 h at 35° C., and subsequently heated for 24 h at 100° C. under static conditions. The solid product obtained after hydrothermal treatment was filtered and dried at 100° C. without washing. The template was removed by calcination at 550° C. for 6 h.

Next, the as-synthesized mesoporous $SiO_2$ powder was loaded close to the bottom of a small quartz tube (diameter: ~1.5 cm), which serves as the inner reactor. The inner tube containing $SiO_2$ template was then placed into the center of an outer quartz tube (diameter: ~2.5 cm) for CVD. Si was deposited at 500° C. and 40 Torr using silane ($SiH_4$) as the Si precursor and hydrogen ($H_2$) as the carrier gas. In a typical synthesis of mesostructured Si, 200 mg of $SiO_2$ template was used, with flow rates of $H_2$ and $SiH_4$ set at 60 and 2 standard cubic centimeters per minute (sccm), and a total CVD duration of 120 min. Subsequent HF (Sigma-Aldrich, USA, 48%) etching for 5-10 min was used to remove the template at room temperature. The etched samples were filtered, rinsed with DI water, isopropanol (IPA) and dried in air. The final product is in brownish powered form.

Electron Microscopy.

Mesostructured Si was sonicated in IPA, and then dispersed onto Si wafers (Nova Electronic Materials, USA, p-type, 0.001 Ω·cm) for scanning electron microscopy (SEM) (Carl Zeiss, Germany, Merlin FE-SEM) and over copper grids (Ted Pella Inc., USA, Lacey Formvar/Carbon, 200 mesh) for transmission electron microscopy (TEM) (FEI, USA, Tecnai F30). The high-angle annular dark field (HAADF) scanning transmission electron microscope (STEM) images were recorded using an aberration corrected STEM (JEOL, Japan, JEM-ARM200CF). The electron-dispersive X-ray spectroscopy (EDX) maps were collected simultaneously with HAADF images using the same microscope equipped with an Oxford X-Max$^N$ 100 TLE windowless SDD X-ray detector (Oxford Instruments, UK). For in-situ heating TEM study, samples were dispersed on molybdenum grids (Structure Probe Inc., USA, Holey Carbon, 200 mesh) and imaged using a JEOL JEM-3010 (JEOL, Japan) with a double-tilt heating stage (Gatan Inc., USA, Model 652). The temperature ramping was set as 50° C./min from ambient to 900° C. Images were taken at room temperature, and at 10 min, 30 min, 60 min, 90 min and 120 min time points at 900° C.

Nitrogen Sorption Measurements.

Nitrogen sorption isotherms were collected on a Micromeritics ASAP 2020 (Micromeritics, USA) surface area and pore size analyzer at 77 K. Pore size distribution was calculated in the Micromeritics ASAP2020 software package (assuming slit pore geometry), using a non-linear density functional theory (NLDFT) model. All samples were degassed at 180° C. overnight prior to experiment. For all measurements, ultra high purity (UHP) grade helium (He) and nitrogen ($N_2$) were used.

Small Angle X-Ray Scattering (SAXS).

SAXS measurements were conducted at the 12ID-B station at the Advanced Photon Source (APS), Argonne National Laboratory (ANL). The wavelength of the X-ray beam was 0.8856 Å, and the beam size was 0.20(H)×0.03 (V) $mm^2$. The detector for SAXS measurements was the Pilatus 2M (DECTRIS Ltd., Switzerland). The exposure time was set to 1 s for all measurements and the sample-to-detector distance was about 2 m, which allows covering scattering momentum transfer, q, up to 1.0 $Å^{-1}$. The q value calibration was performed using silver behenate prior to measurements. The isotropic 2-D images were converted to 1-D scattering profiles using the Matlab software package developed at the beamline. For static SAXS measurements, powder samples were sandwiched with kapton tapes and loaded onto the sample holder. For in-situ heating SAXS measurements, samples were first pelleted and loaded in a Linkam TS1500 heating stage (Linkam Scientific Instruments Ltd., UK). The sample chamber of the heating stage was sealed and purged with $N_2$ during the whole heating process. The temperature ramping rate was set as 60° C./min and the first temperature set point was 800° C. After reaching the set point, the temperature was fixed at 800° C. for 20 min, 900° C. for 20 min and 1000° C. for 20 min, respectively. SAXS data were collected every 38 s. For in-situ stability assays in aqueous systems, 1× phosphate buffered saline solution (PBS) or 0.60 mg/mL collagen hydrogel were added into individual quartz capillary tubes (O.D., 1.5 mm), respectively. Powders were subsequently added into the tubes and mixed with solution or gel to form suspensions at room temperature. Data were collected every 30 min in the first 6 h and every 2 h in the last 6 h.

Transmission X-Ray Microscopy (TXM).

Absorption full-field nano-computed tomography (nano-CT) was performed on the new transmission X-ray microscope at sector 32-ID of APS in ANL. Mesostructured Si was first mounted onto a micromanipulator installed in a focused ion beam (FIB) system (FEI, USA, Nova 600 NanoLab). The micromanipulator was secured on a custom-built holder for data collection. Acquisition was conducted with a monochromatic beam tuned at 8 keV. The condenser and the objective lens used are diffracting optics developed in-house. X-rays are focused to the sample thanks to a beam-shaping condenser (BSC), i.e., a mosaic of diffraction gratings organized in concentric rings. The round BSC can collect a large portion of the beam with its diameter of 1.6 mm. Gratings in each rings have spacing decreasing down to 60 nm at the optic periphery. A 180 µm large Fresnel zone plate with 60 nm outer most zone width was used as a microscope objective lens in order to magnify radiographs of the sample placed on a high accuracy air-bearing rotary stage. With a distance CCD-sample set to 3.4 m, a magnification of ~47 was obtained. The X-ray detection system corresponds to an assembly comprising a scintillator (LuAG), a 5× microscope objective, a 45° mirror and a low noise fast CCD cooled at −40° C. The voxel width obtained in this geometry was 27.6 nm and the field of view was about 70×60 µm$^2$ while the illumination coming from the BSC was a disk slightly larger than 70 µm. The true spatial resolution given by the zone plate is ~60 nm. 3D reconstructions were performed with the software Tomopy (http://www.aps.anl.gov/tomopy/), an open source Python based toolbox for the analysis of synchrotron tomographic data.

The 3D iso-intensity surfaces were constructed and visualized using Amira 5.5 (FEI Visualization Sciences Group). Segmentation of intra- and inter-granular voids was carried out based on intensity. Inter-granular voids were assigned to intensity value less than −0.00015. Intra-granular voids were determined manually by choosing low intensity regions within particles slice by slice using a magic wand tool.

Atom-Probe Tomography (APT).

Mesostructured Si particles were transferred onto Si microposts using a micromanipulator installed in a focused ion beam (FIB) system (FEI, USA, Nova 600 NanoLab). Samples were then mounted and milled into needle-like microtip specimen for APT characterization. The APT was run in an ultraviolet (UV) laser-assisted local-electrode atom-probe (Cameca, USA, LEAP 400XSi). Surface atoms from a microtip were evaporated with an applied voltage of 1~6 kV and the assistance of a 30 pJ UV (wavelength λ=355 nm) laser pulsing at 250 kHz frequency. The mass-to-charge (m/z) ratios of individual evaporated ions and their corresponding (x, y, z) coordinates in space were recorded with a position sensitive detector. The samples were held at 30 K and 2×10$^{-11}$ Torr during APT experiments. The 3D reconstructions and data analyses were performed using Cameca's Integrated Visualization and Analysis Software (IVAS) 3.4 code. Typical regions of both Si nanowires (FIG. 2C, left panel) and micro-bridges (FIG. 2C, right panel) were cropped from FIG. 2B using a region-of-interest (ROI) tool in IVAS. A series of Si isoconcentration surface from 50 at. % to higher concentrations were created for both regions (FIG. 2E), i.e., nanowires and micro-bridges until no isoconcentration surface with higher atomic concentration could be created. Proximity histograms (FIG. 2D) were calculated using the 60% Si isoconcentration surface of the dataset in FIG. 2B, and included information of both Si nanowires and inter-connecting micro-bridges. For histogram shown in FIG. 2E, the number of Si atoms per Si concentration interval was calculated by subtracting the total number Si atoms enclosed within one isoconcentration surface from the precedent isoconcentration surface. For example, the number of Si atoms that is 50~51 at. % is the difference between the total Si atoms enclosed in 50% isoconcentration surface and that in 51% at. %. The Si concentration distribution was plotted by calculating the relative frequency of the number of Si atoms per Si atomic concentration.

Electrical measurements.

Mesostructured Si particles were gently sonicated in IPA and dispersed onto Si substrates (Nova Electronic Materials, 600 nm oxide, p-type, 0.001 Ω·cm) with photo-lithographically patterned gold electrodes. Electrical contacts onto individual Si particles were made with an FIB system (FEI, USA, Nova 600 NanoLab) by depositing platinum (Pt) wires with a built-in gas-injection system (GIS). The electrical conductance measurements were evaluated using a dual-channel source-meter (Keithley 2636A) and a probe station (Rucker & Kolls, Model 680A). The particles were then removed from the interconnects by sonication and the conductance was subsequently measured as controls.

Atomic Force Microscopy (AFM) Measurements.

Force curves were collected using an Asylum MFP-3D AFM (Asylum Research, USA) with ACTA (AppNano, USA, nominal spring constant 40 N/m) probes in air and AC240 (Olympus, Japan, nominal spring constant 2 N/m) probes in liquid. Prior to measurements, the inverse optical lever sensitivity and cantilever spring constant were calibrated following vendor's standard procedures. For all measurements, mesostructured Si particles were first transferred onto Si substrates (Nova Electronic Materials, USA, p-type, 0.001 Ω·cm). Prior to solution phase AFM experiments, samples were also soaked in 1×PBS solution at room temperature for ~2 h. Force curves were recorded by loading at a rate of 1 µm/s up to an indentation depth of ~10 nm, followed by unloading at the same rate. For both measurements in air and in fluid, ten particles were chosen to take force curves by making indentations on random sites over the particle surfaces. The total number of data points is n=138 for the sample in air and n=94 for the sample in liquid. Asylum Research software was used for data collection and analysis. Oliver-Pharr method was used by fitting the range between 25% and 75% of maximum indentation of the retraction curve. The as-calculated value was reduced Young's modulus $E_r$, which was comprised of the indenter and sample's Young's modulus ($E_i$ for indenter, $E_s$ for sample) and Poisson ratio ($v_i$ for indenter, $v_s$ for sample) by $1/E_r=(1-v_i^2)/E_i+(1-v_s^2)/E_s$. The indenter's Poisson's ratio was 0.17 and its Young's modulus was 150 GPa, for both Si cantilevers. The sample's Poisson's ratio was chosen as 0.10 from literature[5]. Based on the equation, $1/E_r=(1-v_i^2)/E_i+(1-v_s^2)/E_s$, it is noted that even an appreciable deviation in the Poisson's ratio will not introduce significant error into the calculated sample modulus[5].

Ultraviolet-Visible (UV-Vis) Spectroscopy.

Prior to measurements, mesostructured Si powders were soaked in 1×PBS for 0 h, 2 h, 12 h and 24 h. After filtration and rinsing with DI water, samples were re-dispersed in IPA and drop casted over glass slides and air dried. The thickness of the Si films was ~20 µm, as determined by a profilometer (Bruker, USA, Dektak XT-S). Diffuse reflectance UV-Vis spectra were collected on a Cary 5000 UV-Vis-NIR spectrometer (Varian, USA) equipped with a diffuse reflectance accessory (DRA). The acquired diffuse reflectance spectra were converted to Kubelka-Munk functions. Tauc plots were then plotted to calculate band gap energies.

Raman Spectroscopy.

Prior to measurements, mesostructured Si powders were soaked in 1×PBS for 0 h, 2 h, 12 h and 24 h. Raman spectra were recorded using a LabRAM HR evolution system (Horiba, Japan), with samples immersed in PBS solutions.

Cell/Si Interface Imaging.

A. High-Pressure Freezing and Freeze-Substitution.

Human umbilical vein endothelial cells (HUVEC) were first seeded on a transwell with 96 permeable supports (Corning Inc., USA, polyester membrane, pore size, 1.0 µm) and cultured in Medium 200 (Life Technologies, USA) until reaching confluency. Mesostructured Si particles (~0.01 mg) were added to the transwell, which settled down within 15 min. The polyester membrane was peeled off from the well and transferred to an aluminum planchet, with excess space filled with 1-hexadecene (Sigma-Aldrich, USA). Samples were frozen in a Baltec HPM 010 high-pressure freezer (Technotrade, USA) and then freeze-substituted in 0.25% glutaraldehyde (Electron Microscopy Sciences, USA) and 0.1% urinal acetate (Electron Microscopy Sciences, USA) dissolved in anhydrous acetone (Electron Microscopy Sciences, USA), using an automated freeze substitution machine (AFS2, Leica Microsystems, Germany). The temperature increased from −180° C. to −80° C. in 12 h and stayed at −80° C. for 72 h. The temperature was then ramped from −80° C. to −20° C. over 12 h. Samples were washed with anhydrous acetone three times at −20° C., then transferred to 4° C., held overnight, and warmed to room temperature. Samples were then infiltrated with increasing concentrations of epoxy resin in anhydrous acetone (low viscosity Spurr, Ted Pella Inc., USA, 20%, 25%, 33%, 50%, and 100%; v/v) and finally solidified at 60° C. for 24 h. Epoxy sections of ~100 nm were cut using a ultramicrotome (Ultracut E, Reichert-Jung, USA) collected on copper grids (Electron Microscopy Sciences, USA, 200 mesh). Sections were stained with 2% (w/v) uranyl acetate and 0.5% (w/v) lead citrate (Electron Microscopy Sciences, USA). Samples were imaged using a Tecnai F30 TEM (FEI, USA).

B. Chemical Fixation.

HUVECs and mesostructured Si mixture were prepared in the same way for freeze substitution on transwell membranes. The samples were fixed with 2% glutaraldehyde and 4% paraformaldehyde (Electron Microscopy Sciences, USA) in 0.1 M sodium cacodylate buffers (Electron Microscopy Sciences, USA) overnight at 4° C. The samples were then washed three times with sodium cacodylate buffers for 5 min each time. After replacing with 1% osmium tetroxide (Electron Microscopy Sciences, USA) in sodium cacodylate buffers and incubating for 60 min, the samples were washed twice with sodium cacodylate buffers for 5 min each time. Maleate buffers (Electron Microscopy Sciences, USA, pH 5.1) were then used to rinse the samples for 5 min. The samples were subsequently stained with 1% uranyl acetate in maleate buffers for 60 min. After the staining, the samples were washed three times with maleate buffers with 5 min each time. The following dehydration process involves a series of washing steps with increasing concentrations of acetone in maleate buffers (25% 2×5 min, 50% 2×5 min, 70% 2×5 min, 95% 2×5 min, 100% 3×15 min; v/v). The infiltration process was performed in the same way as that used in freeze-substitution method (epoxy in anhydrous acetone, 20%, 25%, 33%, 50%, and 100%; v/v). The final epoxy resins were solidified at 60° C. for 24 h. Epoxy sections were cut, stained and imaged in the same way as those used for freeze substitution.

In Vitro Si Degradation.

A series of samples with 50 µg, 100 µg and 300 µg mesostructured Si in 1 mL of 1×PBS solution were incubated at both room temperature and 37° C. An aliquot of 0.5 mL solution was removed at different time points from each tube and diluted with 4.5 mL 2% $HNO_3$ and subjected to analysis by inductively coupled plasma optical emission spectroscopy (710 ICP-OES, Agilent Technologies, USA). 0.5 mL of fresh PBS solutions were added back each time to all tubes. For each group of samples, 5 independent tests were performed (i.e., n=5).

Calcium Imaging.

HUVECs were first cultured on petri dishes to reach a confluency of ~80% before experiments. Cells were stained with 1 µM Fura-2 AM (Life Technologies, USA) for 30 min and washed three times with a HEPES-buffered Tyrode's solution (119 mM NaCl, 5 mM KCl, 25 mM HEPES, 2 mM $CaCl_2$, 2 mM $MgCl_2$, 6 g/L glucose, pH 7.4). Solid silicon particles were prepared by mechanically grinding of a silicon wafer (Silicon Quest, USA, p-type, 1-10 Ωcm). Both mesostructured and solid Si particles were immersed in HEPES-buffered Tyrode's solutions overnight before applying to the stained cell cultures. About 0.01 mg of Si particles were delivered and allowed to settle down for about 5 min to form interfaces with cells. Glass pipettes with tip diameters of ~1.5 µm were pulled in a flaming/brown type micropipette puller (P-97, Sutter Instruments, USA). Micropipettes were filled with the same Tyrode's solution as the bath and controlled with a motorized micromanipulator (PatchStar, Scientifica, UK). In general, only particles sitting on cell bodies, with lateral sizes of ~5 µm, were chosen. Glass pipettes were approached vertically using the micromanipulator and the pipette resistances were monitored in real time. The contact point was determined by the time where a transient or steady increase in the pipette resistance was observed. After making contact with the particles, pipettes were lowered by another 1 µm and held still for 20 s before retraction. During the whole process, fluorescence images were collected using an upright microscope (BX61WI, Olympus, Japan) equipped with an EM-CCD camera (C9100-13, Hamamatsu Photonics, Japan). Images from excitation wavelengths at 340 nm and 380 nm were taken every 1 s. Ratiometric information was obtained from the images collected at 340 nm and 380 nm, and was used for quantitative analysis in MetaFluor software (Molecular Devices, USA). The amplitude and the slope of the ratio changes after mechanical perturbation were defined in FIG. 3E, and statistically compared between porous/mesostructured/amorphous and solid/single crystalline Si samples. The amplitude was calculated as a ratio between the peak ratiometric difference and the baseline. The slope was determined by linear fitting of the range between 25% and 75% of the maximum from baseline.

Cytotoxicity Assays.

HUVEC (Life Technologies, USA), C2C12 cells (ATCC, USA) and human aortic smooth muscle cells (HASMC) (Life Technologies, USA) were seeded in 96-well plates and settled down for 1 d prior to applying mesostructured Si particles. The particles were added to make the final concentration as 0.1 mg/mL in each well. In the positive control groups, no particles were added. On days 1, 3, 5, 7 of the co-culture with Si particles, 3-(4,5-dimethylthiazol-2-yl)-2,5-diphenyltetrazolium bromide (MTT) (Life Technologies, USA) were added and the mixtures were incubated for 4 h at 37° C. Dimethyl sulfoxide (DMSO) (Thermo Fisher Scientific, USA) was added to dissolve the as-formed formazan after all the solutions were removed. After 10 min incubation at 37° C., the absorbance of the DMSO solution in each well was recorded with a multi-plate reader (Tecan Group Ltd., Switzerland, Infinite 200 PRO) at 570 nm. For each group, n=8.

In Vivo Si Biocompatibility and Degradability.

The animal protocol used for this study was in accordance to the policies of the University of Chicago and were approved by the Institutional Animal Care and Use Committee (IACUC). Young adult male CD® IGS rats weighing 226~250 g were ordered from Charles River Laboratories (USA) and housed in pairs in a 6 AM-6 PM light dark cycle. Mesostructured Si and sodium carboxymethyl cellulose (CMC, MW~250,000, Sigma-Aldrich, USA) were sterilized by UV irradiation for 24 h. Si particles were suspended in 1% CMC solution of 1×PBS and sonicated for 1 h before being loaded into 1 mL syringes under sterile conditions. Anesthesia was induced briefly, prior to injection, with isoflurane in 100% oxygen. Each rat received one subcutaneous injection of 5 mg mesostructured Si in 0.5 mL of 1% CMC. 1 day, 7 days and 21 days after the injection, four rats were sacrificed at each time point for examination. Tissues retrieved from the necropsy were fixed in 10% neutral buffered formalin (Sigma-Aldrich, USA), embedded in paraffin, sectioned, and stained with hematoxylin and eosin for histological examination using standard techniques and then reviewed by a pathologist.

Artificial Lipid Bilayer Experiments.

A. Experimental Setup.

An inverted microscope (Zeiss IM35, Germany) was used with a 10×/0.25 NA and a 40×/0.55 NA lens to deliver focused laser pulses with spot sizes in diameter of ~40 μm and ~10 μm, respectively. The beam of the diode-pumped solid-state (DPSS) laser (UltraLaser, Canada) was modulated with an acousto-optic modulator (NEOS Technologies, USA), controlled by transistor-transistor logic (TTL) pulses, delivered individually or in trains of pulses at desired frequencies by a custom-made circuit board. Voltage- and current-clamp protocols were done by an Axopatch 200B amplifier (Molecular Devices, USA), controlled by a personal computer (PC) through a digital-to-analog converter (Innovative Integration SBC-6711-A4D4, USA) with an in-house program control. Analog data were low-pass filtered by an 8-pole Bessel filter (Frequency Devices 950L8L, Canada), converted into digital signal by the same board and acquired by a PC. Patch pipettes were pulled in a $CO_2$ laser micropipette puller (Sutter Instruments P-2000, USA) and polished in a custom-made microforge for a final resistance of 2-4 MΩ when filled with adequate solution. For the temperature measuring experiments, the resistance of a positioned patch pipette was monitored and recorded by an OC-725A amplifier (Warner Instrument, USA). Experiments to measure capacitance change were carried out with a sinusoidal command voltage using a function generator (Krohn-Hite 1200A, USA).

B. Lipid Bilayer Formation.

Asolectin lipids (25 mg/mL in chloroform, soybean polar lipid extract, Avanti Polar Lipids, USA) were smoothed in a test tube to form a thin film, and then dried inside a nitrogen desiccator for about an hour before use. The film was dissolved in n-decane (Thermo-Fisher Scientific, USA) in order to produce a lipid mix with final concentration 25 mg/mL. A custom-made upper chamber containing a 300 μm diameter hole for planar lipid bilayer formation was used and placed in a glass-bottomed lower chamber. Typically, 1 μL of the lipids in n-decane was deposited on the upper chamber hole and let dry for about 15 minutes. Afterwards both chambers were filled with bilayer bath solution (in mM: KCl 90, HEPES 10; pH 7.4). Each chamber was then connected to the patch amplifier headstage through Ag/AgCl hemicells via salt bridges made with 1% ultrapure agar (USB Corp., USA) melted in a solution containing 1M N-methyl-D-glucamine (NMG) (Sigma-Aldrich, USA) and 10 mM HEPES, pH 7.4. A lipid bilayer was painted with an air bubble held by a pipette tip. The formation of the lipid bilayer was monitored under voltage clamp by observing the current responses to a 1V/s voltage ramp. The recording electrode was connected to the lower chamber and the reference electrode was connected to the top chamber. Data was low-pass filtered at 50 kHz by the 8-pole Bessel filter and sampled at 200 kHz.

The material was grinded and sonicated to roughly spherical shape of ~1-2 μm in diameter. Approximately 0.01 mg of mesostructured Si particles were delivered into the upper bath solution and allowed to settle down for about 5 min. Most of the particles sank to the bottom of the upper chamber and made contact with the bilayer. The laser power was adjusted by a set of neutral density filters manually. The laser pulse frequency and duration were controlled by the in-house software and external custom-made hardware. For these experiments we used the 10× objective lens which produced a laser spot size approximately 40 μm in diameter.

C. Capacitance Measurements.

Briefly, the current responses of the bilayer were recorded when a 5 kHz sinusoidal carrier voltage signal was concurrently used as the voltage command, while Si-based film was illuminated by the laser pulses. Upon stimulation, if the bilayer impedance was altered, the magnitude and the phase of the output current would change. Since the impedance is inversely related to the capacitance, an increase in bilayer capacitance due to a temperature rise would lower the impedance, resulting in an increase of output current with the same phase angle with respect to voltage. After low-pass filtered at 20 kHz and sampled at 100 kHz, the sinusoidal current output signals were rectified, and low-pass filtered at a cutoff frequency of 2 kHz. The difference of the current outputs, with and without the laser stimulation, reflects the capacitance change in the bilayer.

D. Local Temperature Measurements.

During the bilayer stimulation experiment, a pipette electrode (2~4 MΩ) filled with bilayer bath solution was placed adjacent to the stimulation site. As the solution inside the pipette was the same as in the bath, the effect of liquid junction potential is diminished, i.e., no ionic gradient across the pipette tip. The resistance of this temperature-monitoring electrode was recorded. After the stimulation experiment, the temperature-monitoring electrode was placed carefully into a chamber with bilayer bath solution pre-heated to about 50° C. A thermocouple was positioned close to the pipette tip. A calibration curve was constructed, based on the pipette resistances in the range of 50 to 20° C. Subsequently, the calibration curve was used to estimate the temperature change from the pipette resistances values recorded earlier.

E. Capacitive Current Recording.

Capacitive currents were recorded in voltage-clamp mode. A laser pulse was delivered to the preparation 300 ms after the voltage was jumped from a holding potential of 0 mV to the desired voltage. The amplifier output was low-pass filtered at 50 kHz and sampled at 200 kHz.

Dorsal Root Ganglia (DRG) Neurons Experiments.

A. DRG Culture.

DRGs were extracted from decapitated P1-P3 Sprague-Dawley rats and were placed immediately in Dulbecco's modified eagle medium (DMEM) (Life Technologies, USA) on ice. The ganglia were transferred to a 0.25% solution of trypsin (Worthington, USA) in Earle's balanced salt solution (EBSS) (in mM: NaCl 132, KCl 5.3, HEPES 10, $NaH_2PO_4$ 1, glucose 5.5; pH 7.4) and placed for 20 min in a 37° C. shaker. Afterwards, the cells were centrifuged and the supernatant was replaced with EBSS added with 10% fetal bovine serum (FBS) (ATCC, USA). After mechanically dispersing the cells with pipetting, they were centrifuged and the supernatant was replaced with DMEM containing 5% FBS. Next, cells were seeded into poly-L-lysine (PLL) (Sigma-Aldrich, USA) coated glass-bottom Petri dishes, and allowed 30 min for cell adhesion. Finally, the dishes were flooded with DMEM supplemented with 5% FBS, 100 U/ml penicillin (Sigma-Aldrich, USA), and 100 µg/ml streptomycin (Sigma-Aldrich, USA), and incubated at a 37° C. chamber with 5% $CO_2$ until used for experiments. The DRG neurons are ready for use in about 3 hours and can be used for experiment for about a week.

The animal protocol used in this step was in accordance to the policies of the University of Chicago and were approved by the Institutional Animal Care and Use Committee (IACUC).

B. Electrophysiology.

Before the experiment, supplemented DMEM in the Petri dish with DRG neurons was rinsed three times with recording solution (in mM: NaCl 132, KCl 4, $MgCl_2$ 1.2, $CaCl_2$ 1.8, HEPES 10, glucose 5.5; pH 7.4). About 0.01 mg of mesostructured Si particles were delivered and settled for approximately 5 min. In general, a DRG neuron with a single particle (size: ~2 µm) attached to the soma was visually selected for patching. Desired neurons were patched with a ~2 MΩ pipette, filled with pipette solution (in mM: NaCl 10, KCl 150, $MgCl_2$ 4.5, EGTA 9, HEPES 10; pH 7.3). Voltage recordings were made in current clamp mode. Every three seconds, a 1 ms suprathreshold amplitude current injection was delivered to the neuron to assess its excitability and followed by a 1 ms laser pulse, 300 ms later. We used the 40× objective lens for these experiments, therefore a 10 µm diameter laser spot was delivered to the preparation. Then the minimal power enough to elicit action potentials (APs) was determined and applied in trains of laser pulses at different frequencies. Spike responses elicited by either individual pulses or pulse trains were low-pass filtered at 5 kHz and sampled at 20 kHz.

C. Data Analysis.

Spike latency was calculated as the time between the onsets of the light pulses and the spike peaks. Jitter was calculated as the standard deviation (SD) of spike latencies, measured either across all the spikes throughout a spike train (throughout trial jitter), or for individual spike across different trials of trains (trial-to-trial jitter). Specifically, 21 spikes were collected at each frequency, and repeated 4 times. To calculate 'throughout trial jitter', SDs of latencies were taken throughout 21 spikes in a single trace, followed by averaging them over 4 trials, To calculate 'trial-to-trial jitter', SDs of latencies were taken for one specific spike (e.g., the second spike in the train) in 4 independent trials, followed by averaging them throughout 21 spikes in a single trace. For all latency and jitter analyses, light pulses which failed to elicit a spike were ignored.

Fast Fourier transform was performed on representative traces for each frequency in OriginPro. Area-based return map, $A_n$-$A_{n+1}$ ($A_n$ is the area of the $n^{th}$ induced neuronal signal)[6], was obtained by plotting the integrated area for each signal (range: peak-10 ms peak+10 ms) using a MATLAB code. Height-based return map was obtained using the amplitude values of each signal in MATLAB. At each frequency, 4 traces were analyzed. For each trace, analysis was performed for spikes from the $2^{nd}$ to the $21^{st}$.

Device Fabrication.

The device was fabricated on a Si substrate (n-type, 0.001~0.005 Ω·cm, Nova Electronic Materials, USA). The fabrication process consists of two steps of photolithography. The first step yields mesostructured Si-covered SU-8 micro-pads. The as-fabricated micro-pads were then connected by a second step of lithography. Briefly, one layer of SU-8 photoresist (SU-8 2002, MichroChem Corp., USA) was first spin-coated on the substrate, followed by baking at 65° C. for 2 min and 95° C. for 4 min, respectively. The SU-8 coated substrate was then photolithographically patterned and post-exposure baked at 65° C. for 2 min and 95° C. for 4 min. Mesostructured Si suspension in IPA was drop casted on the SU-8 layer and dried before developing in the SU-8 developer (MichroChem Corp., USA) for 4 min to reveal the micro-pad array. To connect the micro-pads, the as-formed isolated array was covered with another SU-8 layer. The second layer was baked at 65° C. for 2 min and 95° C. for 4 min. A mask aligner (EVG 620, EVGroup, Austria) was used to make the interconnections between micro-pads followed by post-exposure baking at 65° C. for 2 min and 95° C. for 4 min. The second layer was next developed using the SU-8 developer for 4 min. The final hard baking at 180° C. for 30 min is optional.

Further details and experimental data relating to this Example (including the data referenced as being "not shown" may be found in U.S. provisional patent application No. 62/350,328, the entire contents of which are hereby incorporated by reference.

REFERENCES FOR MAIN PORTION OF EXAMPLE

1 Leigh, C. *Handbook of porous silicon*. 1st edn, (Springer, 2014).
2 Sailor, M. J. Porous *silicon in practice: preparation, characterization, and applications*. (Wiley-VCH: Weinheim, Germany, 2012).
3 Kim, D.-H., Ghaffari, R., Lu, N. S. & Rogers, J. A. Flexible and stretchable electronics for biointegrated devices. *Annual Review of Biomedical Engineering* 14, 113-128, doi:10.1146/annurev-bioeng-071811-150018 (2012).
4 Tian, B. Z. & Lieber, C. M. Synthetic nanoelectronic probes for biological cells and tissues. *Annual Review of Analytical Chemistry* 6, 31-51, doi:10.1146/annurev-anchem-062012-092623 (2013).
5 Cogan, S. F. Neural stimulation and recording electrodes. *Annual Review of Biomedical Engineering* 10, 275-309, doi: 10.1146/annurev.bioeng.10.061807.160518 (2008).
6 Tasciotti, E., Liu, X. W., Bhavane, R., Plant, K., Leonard, A. D., Price, B. K., Cheng, M. M. C., Decuzzi, P., Tour, J. M., Robertson, F. & Ferrari, M. Mesoporous silicon particles as a multistage delivery system for imaging and therapeutic applications. *Nature Nanotechnology* 3, 151-157, doi:10.1038/nnano.2008.34 (2008).
7 Chiappini, C., De Rosa, E., Martinez, J. O., Liu, X., Steele, J., Stevens, M. M. & Tasciotti, E. Biodegradable silicon nanoneedles delivering nucleic acids intracellularly induce localized in vivo neovascularization. *Nature Materials* 14, 532-539, doi:10.1038/nmat4249 (2015).

8 Gu, L., Hall, D. J., Qin, Z. T., Anglin, E., Joo, J., Mooney, D. J., Howell, S. B. & Sailor, M. J. In vivo time-gated fluorescence imaging with biodegradable luminescent porous silicon nanoparticles. *Nature Communications* 4, doi:10.1038/ncomms3326 (2013).

9 Kim, W., Ng, J. K., Kunitake, M. E., Conklin, B. R. & Yang, P. Interfacing silicon nanowires with mammalian cells. *Journal of the American Chemical Society* 129, 7228-7229, doi:10.1021/ja071456k (2007).

10 Hwang, S.-W., Tao, H., Kim, D.-H., Cheng, H., Song, J.-K., Rill, E., Brenckle, M. A., Panilaitis, B., Won, S. M., Kim, Y.-S., Song, Y. M., Yu, K. J., Ameen, A., Li, R., Su, Y., Yang, M., Kaplan, D. L., Zakin, M. R., Slepian, M. J., Huang, Y., Omenetto, F. G. & Rogers, J. A. A Physically transient form of silicon electronics. *Science* 337, 1640-1644, doi:10.1126/science.1226325 (2012).

11 Park, J.-H., Gu, L., von Maltzahn, G., Ruoslahti, E., Bhatia, S. N. & Sailor, M. J. Biodegradable luminescent porous silicon nanoparticles for in vivo applications. *Nature Materials* 8, 331-336, doi:10.1038/nmat2398 (2009).

12 Kim, D.-H., Viventi, J., Amsden, J. J., Xiao, J., Vigeland, L., Kim, Y.-S., Blanco, J. A., Panilaitis, B., Frechette, E. S., Contreras, D., Kaplan, D. L., Omenetto, F. G., Huang, Y., Hwang, K.-C., Zakin, M. R., Litt, B. & Rogers, J. A. Dissolvable films of silk fibroin for ultrathin conformal bio-integrated electronics. *Nature Materials* 9, 511-517, doi:10.1038/nmat2745 (2010).

13 Liu, J., Fu, T.-M., Cheng, Z., Hong, G., Zhou, T., Jin, L., Duvvuri, M., Jiang, Z., Kruskal, P., Xie, C., Suo, Z., Fang, Y. & Lieber, C. M. Syringe-injectable electronics. *Nature Nanotechnology* 10, 629-636, doi:10.1038/nnano.2015.115 (2015).

14 Zhang, A. Q. & Lieber, C. M. Nano-bioelectronics. *Chemical Reviews* 116, 215-257, doi:10.1021/acs.chemrev.5b00608 (2016).

15 Zimmerman, J. F., Murray, G. F., Wang, Y. C., Jumper, J. M., Austin, J. R., II & Tian, B. Z. Free-standing kinked silicon nanowires for probing inter- and intracellular force dynamics. *Nano Letters* 15, 5492-5498, doi:10.1021/acs.nanolett.5b01963 (2015).

16 Wegst, U. G. K., Bai, H., Saiz, E., Tomsia, A. P. & Ritchie, R. O. Bioinspired structural materials. *Nature Materials* 14, 23-36, doi:10.1038/nmat4089 (2015).

17 Chomski, E. & Ozin, G. A. Panoscopic silicon—A material for "all" length scales. *Advanced Materials* 12, 1071-1078, doi: 10.1002/1521-4095(200007)$_{12:14<1071::}$ aid-adma1071>3.0.co;2-j (2000).

18 Bao, Z. H., Weatherspoon, M. R., Shian, S., Cai, Y., Graham, P. D., Allan, S. M., Ahmad, G., Dickerson, M. B., Church, B. C., Kang, Z. T., Abernathy, H. W., Summers, C. J., Liu, M. L. & Sandhage, K. H. Chemical reduction of three-dimensional silica micro-assemblies into microporous silicon replicas. *Nature* 446, 172-175, doi:10.1038/nature05570 (2007).

19 Dai, F., Zai, J. T., Yi, R., Gordin, M. L., Sohn, H., Chen, S. R. & Wang, D. H. Bottom-up synthesis of high surface area mesoporous crystalline silicon and evaluation of its hydrogen evolution performance. *Nature Communications* 5, doi:10.1038/ncomms4605 (2014).

20 Hochbaum, A. I., Gargas, D., Hwang, Y. J. & Yang, P. Single crystalline mesoporous silicon nanowires. *Nano Letters* 9, 3550-3554, doi:10.1021/nl9017594 (2009).

21 Qu, Y., Liao, L., Li, Y., Zhang, H., Huang, Y. & Duan, X. Electrically conductive and optically active porous silicon nanowires. *Nano Letters* 9, 4539-4543, doi: 10.1021/nl903030h (2009).

22 Li, X. & Bohn, P. W. Metal-assisted chemical etching in HF/H(2)O(2) produces porous silicon. *Applied Physics Letters* 77, 2572-2574, doi:10.1063/1.1319191 (2000).

23 Gordon, L. M., Cohen, M. J., MacRenaris, K. W., Pasteris, J. D., Seda, T. & Joester, D. Amorphous intergranular phases control the properties of rodent tooth enamel. *Science* 347, 746-750, doi:10.1126/science.1258950 (2015).

24 Ott, H. C., Matthiesen, T. S., Goh, S. K., Black, L. D., Kren, S. M., Netoff, T. I. & Taylor, D. A. Perfusion-decellularized matrix: using nature's platform to engineer a bioartificial heart. *Nature Medicine* 14, 213-221, doi: 10.1038/nm1684 (2008).

25 Gu, D. & Schuth, F. Synthesis of non-siliceous mesoporous oxides. *Chemical Society Reviews* 43, 313-344, doi:10.1039/c3cs60155b (2014).

26 Wan, Y., Yang, H. F. & Zhao, D. Y. "Host-guest" chemistry in the synthesis of ordered nonsiliceous mesoporous materials. *Accounts of Chemical Research* 39, 423-432, doi:10.1021/ar050091a (2006).

27 Arora, H., Du, P., Tan, K. W., Hyun, J. K., Grazul, J., Xin, H. L., Muller, D. A., Thompson, M. O. & Wiesner, U. Block copolymer self-assembly-directed single-crystal homo- and heteroepitaxial nanostructures. *Science* 330, 214-219, doi:10.1126/science.1193369 (2010).

28 Joo, S. H., Choi, S. J., Oh, I., Kwak, J., Liu, Z., Terasaki, O. & Ryoo, R. Ordered nanoporous arrays of carbon supporting high dispersions of platinum nanoparticles. *Nature* 412, 169-172, doi:10.1038/35084046 (2001).

29 Zhao, D. Y., Feng, J. L., Huo, Q. S., Melosh, N., Fredrickson, G. H., Chmelka, B. F. & Stucky, G. D. Triblock copolymer syntheses of mesoporous silica with periodic 50 to 300 angstrom pores. *Science* 279, 548-552, doi:10.1126/science.279.5350.548 (1998).

30 Richman, E. K., Kang, C. B., Brezesinski, T. & Tolbert, S. H. Ordered mesoporous silicon through magnesium reduction of polymer templated silica thin films. *Nano Letters* 8, 3075-3079, doi:10.1021/nl801759x (2008).

31 Tanaka, K., Maruyama, E., Shimada, T. & Okamoto, H. *Amorphous silicon*. 1st edn, (Wiley, 1999).

32 Freund, L. B. & Suresh, S. *Thin film materials: stress, defect formation and surface evolution*. 1st edn, (Cambridge University Press, 2009).

33 Imperor-Clerc, M., Davidson, P. & Davidson, A. Existence of a microporous corona around the mesopores of silica-based SBA-15 materials templated by triblock copolymers. *Journal of the American Chemical Society* 122, 11925-11933, doi: 10.1021/ja002245h (2000).

34 Minev, I. R., Musienko, P., Hirsch, A., Barraud, Q., Wenger, N., Moraud, E. M., Gandar, J., Capogrosso, M., Milekovic, T., Asboth, L., Torres, R. F., Vachicouras, N., Liu, Q., Pavlova, N., Duis, S., Larmagnac, A., Voeroes, J., Micera, S., Suo, Z., Courtine, G. & Lacour, S. P. Electronic dura mater for long-term multimodal neural interfaces. *Science* 347, 159-163, doi:10.1126/science.1260318 (2015).

35 Lanzani, G. Materials for bioelectronics: Organic electronics meets biology. *Nature Materials* 13, 775-776 (2014).

36 Gautieri, A., Vesentini, S., Redaelli, A. & Buehler, M. J. Hierarchical structure and nanomechanics of collagen microfibrils from the atomistic scale up. *Nano Letters* 11, 757-766, doi:10.1021/nl103943u (2011).

37 Picas, L., Rico, F. & Scheuring, S. Direct measurement of the mechanical properties of lipid phases in supported bilayers. *Biophysical Journal* 102, L1-L3, doi:10.1016/j.bpj.2011.11.4001 (2012).

38 Han, D. X., Lorentzen, J. D., Weinberg-Wolf, J., McNeil, L. E. & Wang, Q. Raman study of thin films of amorphous-to-microcrystalline silicon prepared by hot-wire chemical vapor deposition. *Journal of Applied Physics* 94, 2930-2936, doi:10.1063/1.1598298 (2003).

39 Li, L., Connors, M. J., Kolle, M., England, G. T., Speiser, D. I., Xiao, X. H., Aizenberg, J. & Ortiz, C. Multifunctionality of chiton biomineralized armor with an integrated visual system. *Science* 350, 952-956, doi:10.1126/science.aad1246 (2015).

40 Shapiro, M. G., Homma, K., Villarreal, S., Richter, C. P. & Bezanilla, F. Infrared light excites cells by changing their electrical capacitance. *Nature Communications* 3, doi:10.1038/ncomms1742 (2012).

41 Carvalho-de-Souza, J. L., Treger, J. S., Dang, B., Kent, S. B. H., Pepperberg, D. R. & Bezanilla, F. Photosensitivity of neurons enabled by cell-targeted gold nanoparticles. *Neuron* 86, 207-217, doi:10.1016/j.neuron.2015.02.033 (2015).

42 Sanders, A. W., Jeerage, K. M., Schwartz, C. L., Curtin, A. E. & Chiaramonti, A. N. Gold nanoparticle quantitation by whole cell tomography. *ACS Nano* 9, 11792-11799, doi:10.1021/acsnano.5b03815 (2015).

43 Liu, Y., Ai, K., Liu, J., Deng, M., He, Y. & Lu, L. Dopamine-melanin colloidal nanospheres: An efficient near-infrared photothermal therapeutic agent for in vivo cancer therapy. *Advanced Materials* 25, 1353-1359, doi:10.1002/adma.201204683 (2013).

44 Kaplan, D. T., Clay, J. R., Manning, T., Glass, L., Guevara, M. R. & Shrier, A. Subthreshold dynamics in periodically stimulated squid giant axons. *Physical Review Letters* 76, 4074-4077, doi:10.1103/PhysRevLett.76.4074 (1996).

45 Liu, Y., Ai, K. & Lu, L. Polydopamine and its derivative materials: Synthesis and promising applications in energy, environmental, and biomedical fields. *Chemical Reviews* 114, 5057-5115, doi:10.1021/cr400407a (2014).

46 Pan, L., Yu, G., Zhai, D., Lee, H. R., Zhao, W., Liu, N., Wang, H., Tee, B. C. K., Shi, Y., Cui, Y. & Bao, Z. Hierarchical nanostructured conducting polymer hydrogel with high electrochemical activity. *Proceedings of the National Academy of Sciences of the United States of America* 109, 9287-9292, doi:10.1073/pnas.1202636109 (2012).

47 Ghezzi, D., Antognazza, M. R., Dal Maschio, M., Lanzarini, E., Benfenati, F. & Lanzani, G. A hybrid bioorganic interface for neuronal photoactivation. *Nature Communications* 2, doi:10.1038/ncomms1164 (2011).

48 Tee, B. C. K., Chortos, A., Berndt, A., Nguyen, A. K., Tom, A., McGuire, A., Lin, Z. C., Tien, K., Bae, W.-G., Wang, H., Mei, P., Chou, H.-H., Cui, B., Deisseroth, K., Ng, T. N. & Bao, Z. A skin-inspired organic digital mechanoreceptor. *Science* 350, 313-316, doi:10.1126/science.aaa9306 (2015).

49 Tian, B. Z, Liu, J., Dvir, T., Jin, L., Tsui, J. H., Qing, Q., Suo, Z., Langer, R., Kohane, D. S. & Lieber, C. M. Macroporous nanowire nanoelectronic scaffolds for synthetic tissues. *Nature Materials* 11, 986-994, doi:10.1038/nmat3404 (2012).

50 Karzbrun, E., Tayar, A. M., Noireaux, V. & Bar-Ziv, R. H. Programmable on-chip DNA compartments as artificial cells. *Science* 345, 829-832, doi:10.1126/science.1255550 (2014).

REFERENCES FOR METHODS II

1 Zhao, D. Y., Feng, J. L., Huo, Q. S., Melosh, N., Fredrickson, G. H., Chmelka, B. F. & Stucky, G. D. Triblock copolymer syntheses of mesoporous silica with periodic 50 to 300 angstrom pores. *Science* 279, 548-552, doi:10.1126/science.279.5350.548 (1998).

2 Sayari, A., Han, B. H. & Yang, Y. Simple synthesis route to monodispersed SBA-15 silica rods. *Journal of the American Chemical Society* 126, 14348-14349, doi:10.1021/ja0478734 (2004).

3 Katiyar, A., Yadav, S., Smirniotis, P. G. & Pinto, N. G. Synthesis of ordered large pore SBA-15 spherical particles for adsorption of biomolecules. *Journal of Chromatography A* 1122, 13-20, doi:10.1016/j.chroma.2006.04.055 (2006).

4 Kleitz, F., Choi, S. H. & Ryoo, R. Cubic Ia3d large mesoporous silica: synthesis and replication to platinum nanowires, carbon nanorods and carbon nanotubes. *Chemical Communications*, 2136-2137, doi:10.1039/b306504a (2003).

5 Bellet, D., Lamagnere, P., Vincent, A. & Brechet, Y. Nanoindentation investigation of the Young's modulus of porous silicon. *Journal of Applied Physics* 80, 3772-3776, doi:10.1063/1.363305 (1996).

6 Kaplan, D. T., Clay, J. R., Manning, T., Glass, L., Guevara, M. R. & Shrier, A. Subthreshold dynamics in periodically stimulated squid giant axons. *Physical Review Letters* 76, 4074-4077, doi:10.1103/PhysRevLett.76.4074 (1996).

7 McGuire, G. E. *Semiconductor materials and process technology handbook*. (William Andrew Publishing/Noyes, 1988).

8 Zink, B. L., Pietri, R. & Hellman, F. Thermal conductivity and specific heat of thin-film amorphous silicon. *Physical Review Letters* 96, doi: 10.1103/PhysRevLett.96.055902 (2006).

9 Cahill, D. G., Katiyar, M. & Abelson, J. R. Thermal conductivity of a-Si: H thin films. *Physical Review B* 50, 6077-6081, doi: 10.1103/PhysRevB.50.6077 (1994).

10 Kovalev, D., Polisski, G., BenChorin, M., Diener, J. & Koch, F. The temperature dependence of the absorption coefficient of porous silicon. *Journal of Applied Physics* 80, 5978-5983, doi:10.1063/1.363595 (1996).

11 Barisik, M. & Beskok, A. Temperature dependence of thermal resistance at the water/silicon interface. *International Journal of Thermal Sciences* 77, 47-54, doi: 10.1016/j.ijthermalsci.2013.10.012 (2014)

12 Shapiro, M. G., Homma, K., Villarreal, S., Richter, C. P. & Bezanilla, F. Infrared light excites cells by changing their electrical capacitance. *Nature Communications* 3, doi:10.1038/ncomms1742 (2012).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A silicon-based material comprising an aggregate of particles, the particles comprising an ordered array of nanostructures, the nanostructures comprising amorphous silicon and oxygen, wherein at least some pairs of adjacent nanostructures are connected by one or more bridges comprising amorphous silicon and oxygen, the one or more bridges extending from the surface of one nanostructure of the pair to the surface of the other nanostructure in the pair, wherein the oxygen resides at or near the surface of the nanostructures and the one or more bridges, and wherein the silicon content of the nanostructures is greater than the silicon content of the one or more bridges.

2. The material of claim 1, wherein the particles are microparticles.

3. The material of claim 1, wherein the particles are irregularly shaped particles, wheat-shaped particles, rods, spheres or combinations thereof.

4. The material of claim 1, wherein the surfaces of the particles define a plurality of pores distributed throughout the material.

5. The material of claim 4, wherein the plurality of pores comprise intergranular pores, intragranular pores and additional pores defined by surfaces of the nanostructures.

6. The material of claim 4, wherein the porosity of the material is at least about 40%.

7. The material of claim 1, wherein the nanostructures are elongated nanostructures.

8. The material of claim 7, wherein the nanostructures are substantially aligned along their longitudinal axes.

9. The material of claim 7, wherein the nanostructures exhibit hexagonal packing or gyroidal packing.

10. The material of claim 7, wherein the one or more bridges are substantially orthogonal to the longitudinal axes of the elongated nanostructures to which the one or more bridges are connected.

11. The material of claim 1, wherein the nanostructures consist essentially of silicon and oxygen.

12. The material of claim 1, wherein the material is characterized by a Young's modulus of no more than about 10 GPa as determined in a dry state.

13. A single particle of the material of claim 1.

14. A method of making a silicon-based material of claim 1, the method comprising exposing a mesoporous silica template to a silicon precursor under conditions to deposit silicon on the surfaces of the mesoporous silica template via chemical vapor deposition (CVD); and removing the mesoporous silica template to provide the silicon-based material.

15. A method of using the silicon-based material of claim 1, the method comprising positioning the Si-based material or a single particle of the material in the vicinity of a lipid bilayer; and illuminating the Si-based material or the single particle with light to produce a photothermal response in the Si-based material or the single particle.

16. The method of claim 15, wherein the lipid bilayer is part of an excitable cell and the photothermal response induces a capacitance increase in the lipid bilayer sufficient to trigger an action potential in the excitable cell.

17. The method of claim 16, wherein the light is pulsed, thereby triggering a spike train.

* * * * *